(12) United States Patent
Starzewski et al.

(10) Patent No.: US 6,423,659 B1
(45) Date of Patent: *Jul. 23, 2002

(54) π-COMPLEX COMPOUNDS

(75) Inventors: Karl-Heinz Aleksander Ostoja Starzewski, Bad Vilbel (DE); Warren Mark Kelly, Airdrie (CA)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/402,263

(22) PCT Filed: Mar. 25, 1998

(86) PCT No.: PCT/EP98/01745

§ 371 (c)(1),
(2), (4) Date: Oct. 1, 1999

(87) PCT Pub. No.: WO98/45339

PCT Pub. Date: Oct. 15, 1998

(30) Foreign Application Priority Data

Apr. 5, 1997 (DE) .......................... 197 14 058

(51) Int. Cl.[7] .................. B01J 31/00; C07F 17/00; C08F 4/64

(52) U.S. Cl. .............. 502/103; 502/117; 502/120; 502/152; 526/133; 526/134; 526/160; 526/161; 526/348.2; 526/352; 526/943; 534/11; 534/15; 556/7; 556/8; 556/14; 556/20; 556/27; 568/1; 568/8; 568/12

(58) Field of Search ............... 556/7, 8, 14, 20, 556/27; 568/1, 8, 12, 502, 103, 117, 120, 152; 526/160, 943, 133, 134, 161, 352, 348.6; 534/11, 15

(56) References Cited

U.S. PATENT DOCUMENTS 6,184,320 B1 * 2/2001 Starzewski et al. ......... 526/161

FOREIGN PATENT DOCUMENTS

| EP | 0 129 368 | 7/1989 |
|---|---|---|
| EP | 0 704 461 | 4/1996 |
| WO | 94/20506 | 9/1994 |

* cited by examiner

Primary Examiner—Porfirio Nazario-Gonzalez
(74) Attorney, Agent, or Firm—Joseph C. Gil; Noland J. Cheung

(57) ABSTRACT

π-complex compounds and in particular metallocene compounds of formula (Ia)(Ib), in which πI and πII represent π-systems, D designates a donor atom and A designates an acceptor atom, D and A being linked by a reversible coordinative bond such that the donor group assumes a positive (partial) charge and the acceptor group assumes a negative (partial) charge, at least one of D and A being part of the associated π-system in each case, M stands for a transition metal of the 3rd, 4th, 5th or 6th subgroup of the (Mendelian) periodic system of elements, X designates an anion equivalent and n designates the number zero, one, two three or four depending on the charges of M and those of πI and πII, are novel and can be used as catalysts for the (co)polymerization of olefins, i-olefins, alkines and/or diolefins or for ring-opening polyaddition.

24 Claims, 1 Drawing Sheet

π-COMPLEX COMPOUNDS

FIELD OF THE INVENTION

Figure 1:
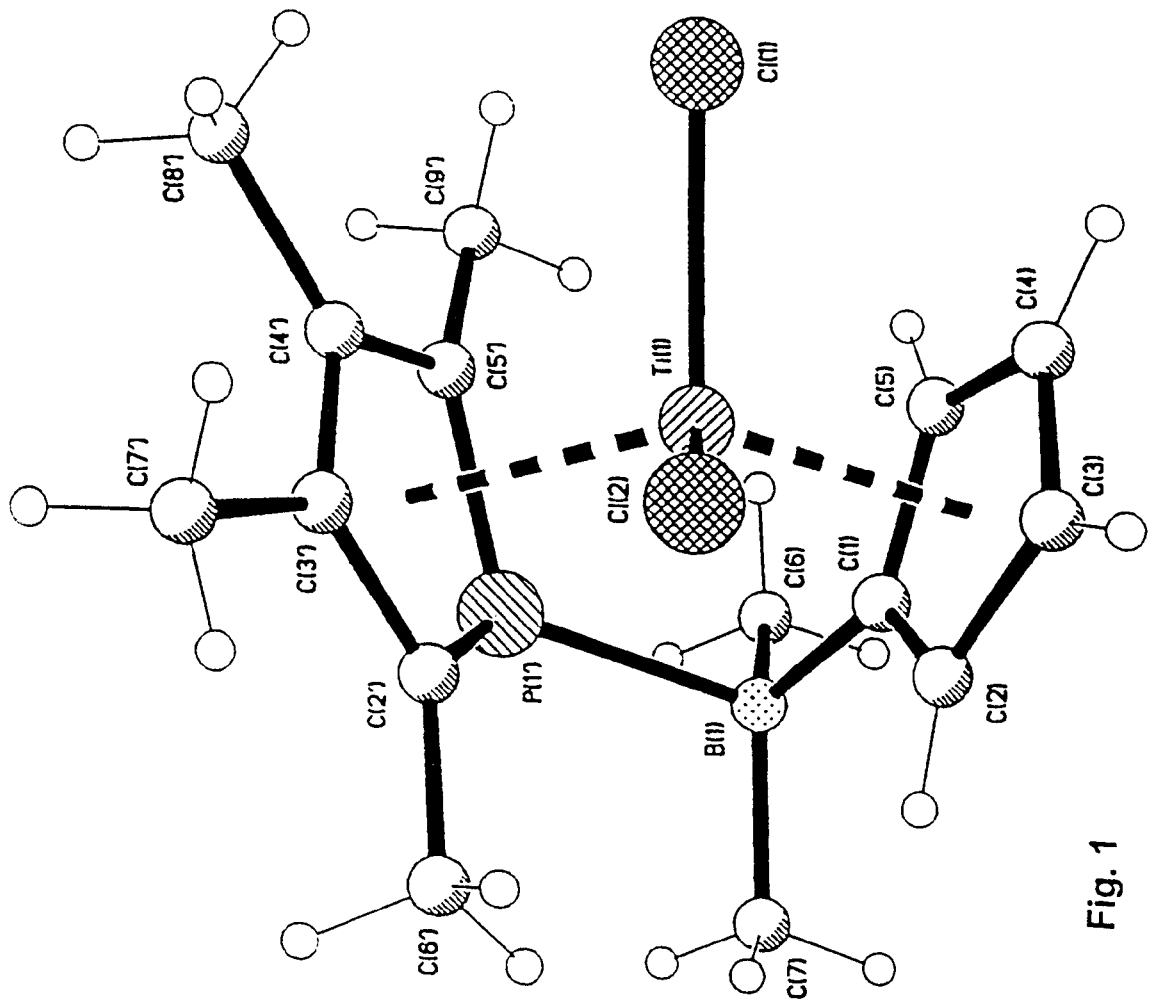

The present invention relates to compounds in which a transition metal is complexed with two π systems. particularly with aromatic π systems (metallocenes), and the two systems are reversibly joined to each other by at least one bridge comprising a donor and an acceptor, wherein at least one of the donor or acceptor atoms is part of the associated π system in each case. The coordinate bond which is formed between the donor atom and the acceptor atom produces a positive (partial) charge on the donor group and produces a negative (partial) charge on the acceptor group:

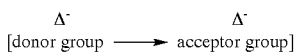

The present invention further relates to the use of these new π-complex compounds, particularly of new metallocenes. as polymerisation catalysts.

BACKGROUND OF THE INVENTION

Metallocenes have long been known as π-complex compounds, as has their use in the polymerisation of olefines (EP-A 129 368 and the literature cited therein). Furthermore, it is known from EP-A 129 368 that metallocenes, in combination with aluminium alkyl/water systems as co-catalysts, constitute effective systems for the polymerisation of ethylene (thus, for example, methylaluminoxane= MAO is formed from about 1 mole of trimethylaluminium and 1 mole of water. Other stoichiometric ratios have also been successfully used (WO 94/20506)). Moreover, metallocenes are already known which comprise cyclopentadienyl skeletons which are covalently linked to each other by a bridge. As an example of the numerous patents and patent applications in this field, EP-A 704 461 should be mentioned, wherein the linking group cited therein constitutes a (substituted) methylene group or ethylene group, a silylene group, a substituted silylene group, a substituted germylene group or a substituted phosphine group. In EP-A 704 461, bridged metallocenes are also provided as polymerisation catalysts for olefines. Despite the numerous patents and patent applications in the field, there is a continuing desire for improved catalysts which are distinguished by a high activity, so that the amount of catalyst remaining in the polymer is small, and which at the same time are suitable for the polymerisation and copolymerisation of olefines to form thermoplastics and to form elastomeric products, and which are also suitable for the polymerisation and copolymerisation of diolefines optionally with olefines.

SUMMARY OF THE INVENTION

It has now been found that particularly advantageous catalysts can be produced which comprise bridged π-complex compounds. particularly metallocene compounds, in which the bridge between the two π systems is produced by one, two or three reversible donor-acceptor bonds, and in which a coordinate bond or what is termed a dative bond is formed in each case between the donor atom and the acceptor atom, on which coordinate bond an ionic bond is superimposed, at least formally, and in which at least one of the donor or acceptor atoms is part of the associated π system in each case. In addition to the bridged state denoted by the arrow between D and A, the reversibility of the donor-acceptor bond also permits the unbridged state, in which, as a result of the rotational energy inherent in them, the two π systems can rotate in relation to each other, by 360 degrees of angle for example, without the integrity of the metal complex being lost. After a complete rotation, the donor-acceptor bond "snaps in" again. In the presence of a plurality of donors and/or acceptors, a "snapping-in" process such as this can even occur after less than 360 degrees of angle have been traversed. Metallocenes according to the present invention can therefore only be represented by a double arrow, and partial formulae (Ia) and (Ib) represent the inclusion of both these states.

Accordingly, the present invention relates to π complex compounds. and particularly metallocene compounds of formula

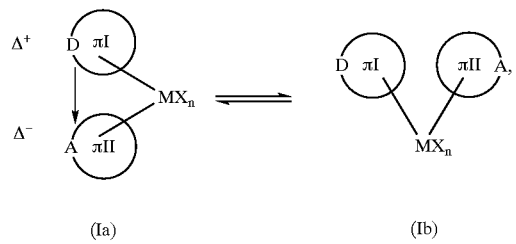

(I)

(Ia)  (Ib)

wherein
πI and πII represent π systems which bear charges which are different from each other or which are electrically neutral, and which can be singly- or doubly-condensed with unsaturated or saturated five- or six-membered rings, D denotes a donor atom which is a substituent of πI or is part of the π system of πI, and which has at least one free electron pair available in its respective bonding state, A denotes an acceptor atom which is a substituent of πII or is part of the π system of πII, and which has an electron pair vacancy in its respective bonding state, wherein D and A are linked by a reversible coordinate bond in such a way that the donor group assumes a positive (partial) charge and the acceptor group assumes a negative (partial) charge, and wherein at least one of D and A is part of the associated π system in each case, wherein D and A themselves may comprise substituents,
wherein each π system or each condensed-on ring system can contain one or more D or A entities, or D and A entities, and wherein in πI and πII, in the non-condensed or in the condensed form, one to all of the H atoms of the π system, independently of each other, can be substituted by identical or different radicals from the group comprising a linear or branched $C_1$–$C_{20}$ alkyl which can be substituted singly to completely by halogens, can be substituted singly to three-fold by phenyl or can be substituted singly to three-fold by vinyl; a $C_6$–$C_{12}$ aryl, and a halogenoaryl comprising 6 to 12 C atoms; and said H atoms can also be singly- or doubly-substituted by D and A, so that the reversible coordinate D→A bond is formed (i) between D and A, which both constitute parts of the respective π system, or (ii) from the D or A part of the π system and the other substituent of the non-condensed π system or of the condensed-on ring system in each case, or (iii) both D and A are such substituents, wherein in the case of (iii) at least one additional D or A entity or both is (are) part of the π system or of the condensed-on ring system, M represents a transition metal of subgroups III, IV, V or VI of the periodic table of the elements (Mendeleev), including the lanthanides and actinides, X denotes an anion equivalent, and n denotes the numbers zero, one, two, three or four depending on the charge of M and on those of πI and πII.

DETAILED DESCRIPTION OF THE INVENTION

In FIG. 1, the structure of dimethylboranyl-cyclopentadienyl-tetramethylphospholyl-titanium tetrachloride is illustrated as an example (see the Examples).

π systems according to the invention comprise substituted and unsubstituted ethylene, allyl, pentadienyl, benzyl, butadiene, benzene, the cyclopentadienyl anion, and species which are formed by the replacement of at least one C atom by a hetero atom. Of the aforementioned species, cyclic species are preferred. The type of coordination of ligands (π systems) such as these to the metal can be of the σ type or of the π type.

π-complex compounds of formula (I) in which the π systems are cyclic and aromatic (metallocenes), can be prepared, for example, either by the reaction of a compound each of formulae (II) and (III)

(II)

(III)

or by the reaction of a compound each of formulae (IV) and (V)

(IV)

(V)

or by the reaction of a compound each of formulae (VI) and (VII)

(VI)

(VII)

with the separation of M'X in the presence or absence of an aprotic solvent, or by the reaction of a compound each of formulae (VIII) and (III)

(VIII)

(III)

or by the reaction of a compound each of formulae (IV) and (IX)

(IV)

(IX)

or by the reaction of a compound each of formulae (X) and (VII)

(X)

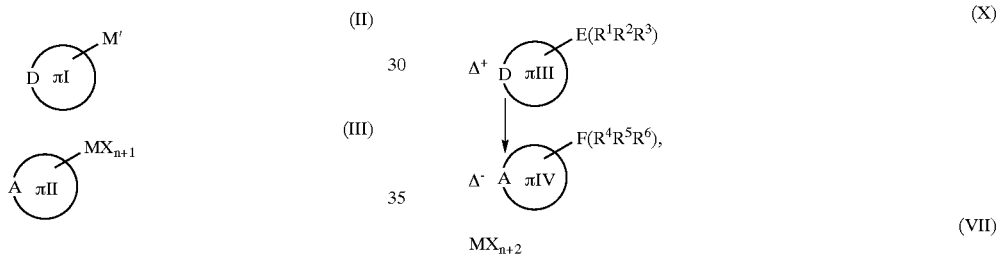

(VII)

with the separation of $E(R^1R^2R^3)X$ and $F(R^4R^5R^6)X$ in the absence or presence of an aprotic solvent, wherein πI, πII, D, A M, X and n have the meanings given above, πIII and πIV represent two different uncharged π systems with a structure corresponding to πI or πII, M' denotes a cation equivalent of an alkali or alkaline earth metal or Tl, E and F, independently of each other, denote one of the elements Si, Ge or Sn, and $R^1$, $R^2$, $R^3$, $R^4$, $R^5$ and $R^6$, independently of each other, represent a straight chain or branched $C_1$–$C_{20}$ alkyl or $C_6$–$C_{12}$ aryl, or a $C_1$–$C_6$ alkyl-$C_6$–$C_{12}$ aryl, a $C_6$–$C_{12}$ aryl-$C_1$–$C_6$alkyl, vinyl, allyl or a halogen, wherein, moreover, in formulae (VIII), (IX) and (X), hydrogen can be present instead of $E(R^1R^2R^3)$ and $F(R^4R^5R^6)$, X can also represent an amide anion of the $R_2N^\ominus$ type or a carbanion of the $R_3C^\ominus$ type, or an alcoholate anion of the $RO^\ominus$ type, and wherein it is possible in addition to react compounds of formulae (II) or (VIII) in the presence of compounds of formulae (V) or (IX) directly with a transition metal compound of formula (VII), Furthermore, two X anions can be joined to form a dianion, optionally with a single- or multi-atom bridge interposed therebetween.

In the last-mentioned variant of the reaction of (VIII) with (III) or of (IV) with (IX) or of (X) with (VII), structure (I) is formed with the separation of an amine $R_2NH$ or $R_2NE$ ($R^1R^2R^3$) or $R_2NF(R^4R^5R^6)$ or of a hydrocarbon compound of formula $R_3CH$ or $R_3CE(R^1R^2R^3)$ or $R_3CF(R^4R^5R^6)$ or of an ether $ROE(R^1R^2R^3)$ or $ROF(R^4R^5R^6)$, wherein the organic radicals R are identical to or different from each other and, independently of each other, represent a $C_1$–$C_{20}$ alkyl, a $C_6$–$C_{12}$ aryl, or a substituted or unsubstituted allyl, benzyl, or hydrogen. Examples of the amine, ether, hydrocarbon, silane, stannane or germane which is separated include dimethylamine, diethylamine, di-(n-propyl)-amine, di-(isopropyl)-amine, di-(tertiary-butyl)-amine, tertiary butylamine, cyclohexylamine, aniline, methyl-phenyl-amine, di-(allyl)-amine or methane, and toluene, xylene, trimethylsilylamine, trimethyl silyl ether, tetramethylsilane and the like, for instance.

It is also possible to react compounds of formulae (II) or (VIII), in the presence of compounds of formulae (V) or (IX), directly with a transition metal compound of formula (VII).

The preparation of open-chain π-complex compounds is effected by methods known to one skilled in the art, with the incorporation of donor and acceptor groups.

The present invention further relates to the use of the complex compounds described above in a method for the homo- or copolymerisation of one or more olefines, i-olefines, alkynes or diolefines as monomers, or for ring-opening addition polymerisation in a gaseous, solution, bulk, high-pressure or slurry phase at −60 to +250° C. preferably up to +200° C. and at 0.5 to 5000 bar, preferably 1 to 3000 bar, and in the presence or absence of saturated or aromatic hydrocarbons or of saturated or aromatic halogenated hydrocarbons and in the presence or absence of hydrogen. wherein said π-complex compounds are used as catalysts in an amount of $10^1$ to $10^{12}$ moles of all the monomers per mole of π-complex, and wherein in addition the polymerisation can be conducted in the presence of Lewis acids, Brönsted acids or Pearson acids, or can also be conducted in the presence of Lewis bases.

Examples of Lewis acids include boranes or alanes, such as aluminium alkyls, aluminium halides, aluminium alcoholates, organoboron compounds, boron halides, esters of boric acid or boron or aluminium compounds which contain both halide substituents and alkyl, aryl or alcoholate substituents, as well as mixtures thereof, or the triphenyl-methyl cation. Aluminoxanes or mixtures of aluminium-containing Lewis acids with water are particularly preferred. According to current knowledge, all acids act as ionising agents which form a metallocenium cation, the charge of which is compensated for by a bulky, poorly coordinating anion.

The present invention also relates to the reaction products of ionising agents such as these with π-complexes of formula (I). These reaction products correspond to formula (XI):

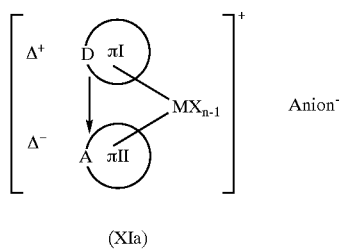

(XIa)

or

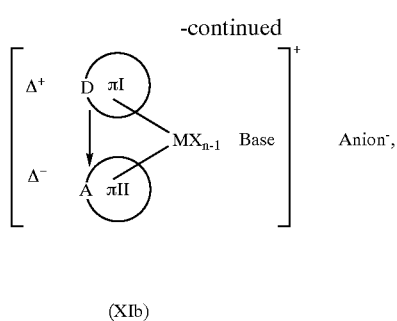

(XIb)

wherein
Anion represents the entire, bulky, poorly coordinating anion and Base represents a Lewis base.

The metallocene compounds of formula (I) can exist in monomeric, dimeric or oligomeric form.

Examples of poorly coordinating anions include:

$B(C_6H_5)_4$, $B(C_6F_5)_4$, $B(CH_3)(C_6F_5)_3$,

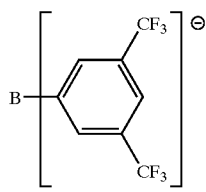

or sulphonates such as tosylates or triflates, tetrafluoroborates, hexafluorophosphates or -antimonates, perchlorates and voluminous cluster molecule anions of the carborane type, for example $C_2B_9H_{12}^{\ominus}$ or $CB_{11}H_{12}^{\ominus}$. In the presence of anions such as these π-complex compounds can act as highly effective polymerisation catalysts even in the absence of aluminoxanes. This situation primarily exists if one X ligand constitutes an alkyl group or benzyl. It can, however, be advantageous to use π-complexes such as these, which comprise voluminous anions, in combination with aluminium alkyls such as $(CH_3)_3Al$, $(C_2H_5)_3Al$, (n-/i-propyl)$_3$ Al, (n-/t-butyl)$_3$Al or (i-butyl)$_3$Al, isomeric pentyl, hexyl or octyl aluminium alkyls, or with lithium alkyls such as methyl-Li, benzyl-Li, butyl-Li or the corresponding organo-Mg compounds, such as Grignard compounds, or organo-Zn compounds. Metal alkyls such as these firstly transfer alkyl groups to the central metal, and secondly they act as scavengers which remove water or catalyst poisons from the reaction medium or monomer during polymerisation reactions. Examples of boron compounds from which anions such as these are derived include:

triethylammonium tetraphenylborate,
tripropylammonium tetraphenyl borate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl(2,4,6-trimethylaluminium) tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate.
tri(sec-butyl)ammonium tetrakis(pentafluorophenyl) borate, N,N-dimethylanilinium tetrakis(pentafluorophenyl) borate,
N,N-diethylaluminium-tetrakis(pentafluorophenyl) borate,
N,N-dimethyl(2,4,5-trimethylaluminium)tetrakis (pentafluorophenyl)borate,
trimethylammonium tetrakis(2,3,4,6-tetrafluorophenyl) borate,
triethylammonium tetrakis(2,3,4,6-tetrafluorophenyl) borate,
tripropylammonium tetrakis(2,3,4,6-tetrafluorophenyl) borate,
tri(n-butyl)ammonium tetrakis(2,3,4,6-tetrafluorophenyl) borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-diethylanilinium tetrakis(2,3,4,6-tetrafluorophenyl) borate,
N,N-dimelthye-(2,4,6-trimethyl(anilinium)-tetrakis-(2,3,4,6-tetraflurophenylborate)dialkylammonium salts, such as:
di-(i-propyl)ammonium tetrakis(pentafluorophenyl) borate and
dicyclohexylammonium -tetrakis(pentafluorophenyl) borate,
tri-substituted phosphonium salts, such as:
triphenylphosphonium tetrakis(pentafluorophenyl)borate,
tri(o-tolyl)phosphonium tetrakis(pentafluorophenyl) borate,
tri(2,6-dimethylphenyl)phosphonium tetrakis (pentafluorophenyl)borate,
tritolylmethyl tetrakis(pentafluorophenyl)borate,
triphenylmethyl tetraphenylborate (trityl tetraphenylborate),
trityl tetrakis(pentafluorophenyl)borate,
silver tetrafluoroborate,
tris(pentafluorophenyl)borane,
tris(trifluoromethyl)borane.

The π-complex compounds or metallocene compounds according to the invention can be used for (co) polymerisation after they have been isolated as the pure substances. It is also possible, however, to produce and use them "in situ" in the (co)polymerisation reactor in the manner known to one skilled in the art.

The π-complex compounds according to the invention are characterised by the presence of at least one coordinate bond between the donor atom(s) D and the acceptor atom(s) A. Both D and A can be substituents of the πI or πII π systems which are associated with them, or can be part of the π system, wherein at least one of D and A is part of the π system, however. The π system here is to be understood as the entire system which is optionally singly- or doubly-condensed. The following embodiments result therefrom:

D is part of the π system, A is a substituent of the π system;

D is a substituent of the π system, A is part of the π system;

D and A are parts of their respective π system.

The following are examples of heterocyclic ring systems in which D or A are part of the ring system:

 (a)

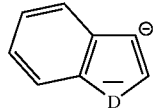 (b)

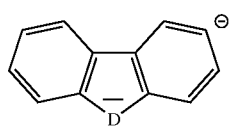 (c)

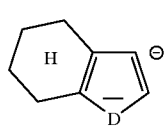 (d)

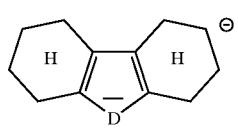 (e)

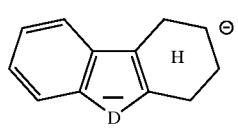 (f)

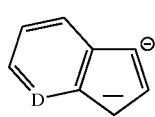 (g)

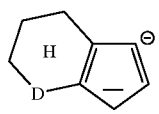 (h)

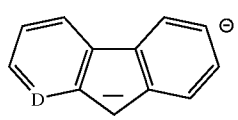 (i)

 (j)

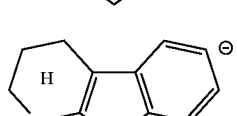 (k)

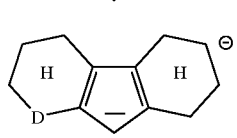 (l)

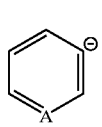 (m)

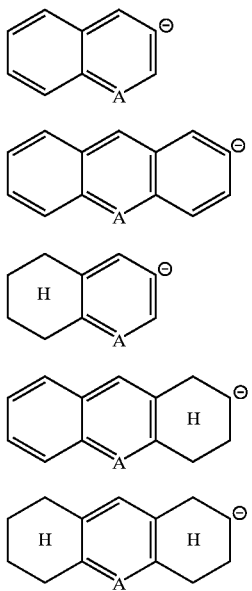

The important heterocyclic ring systems are the systems denoted by (a), (b), (c), (d), (g), (m), (n) and (o); those systems denoted by (a), (b), (c) and (m) are particularly important.

If one of D and A is a substituent of its associated ring system, the ring, system is a 3-, 4-, 5-, 6-, 7- or 8-membered ring system, with or without an electrical charge, which can be further substituted and/or condensed in the manner described, 5- and 6-membered ring systems are preferred. The negatively charged cyclopentadienyl system is particularly preferred.

The first or second π system, namely πI and πII respectively, if it is formed as a ring system and if one of D and A is a substituent of the ring system may for example be one of the group comprising cyclopentadiene, substituted cyclopentadiene, indene. substituted indene, fluorene and substituted fluorene. Substituents can replace one to all of the H atoms of the ring system. These substituents may be a $C_1$–$C_{20}$ alkyl such as methyl, ethyl, propyl, isopropyl, butyl or iso-butyl, t-butyl, hexyl, octyl, decyl, trimethylsilyl, pentamethyldisilanyl, trimethylsilyl-methyl, dodecyl, hexadecyl, octadecyl or eicosyl, a $C_6$–$C_{12}$ aryl such as phenyl, a $C_1$–$C_4$ alkylphenyl, such as tolyl, ethylphenyl, (i-)propylphenyl, (i-,tert.-)butyl phenyl or xylyl, a halogenoaryl, such as fluoro-, chloro- or bromophenyl, naphthyl or biphenylyl, or a triorganyl-silyl such as trimethylsilyl (TMS), or ferrocenyl, as well as D or A as defined above. Condensed-on rings can be either unsaturated, e.g. aromatic rings, or can be partially or completely hydrogenated, so that only the double bond remains which is shared by both the condensed-on ring and the cyclopentadiene ring. Furthermore, benzene rings as in indene or fluorene may contain one or two further condensed-on benzene rings. In addition to this, the cyclopentadienyl ring and a condensed-on benzene ring may jointly contain a further benzene ring which is condensed on.

In the form of their anions, cyclopentadiene skeletons are excellent ligands for transition metals, wherein each cyclopentadienyl carbanion of the aforementioned, optionally substituted form compensates for a positive charge of the central metal in the complex Individual examples of carbanions such as these include: cyclopentadienyl, methyl-cyclopentadienyl 1,2-dimethyl-cyclopentadienyl, 1,3-dimethyl-cyclopentadienyl, indenyl, phenylindenyl, 1,2-diethyl-cyclopentadienyl, tetramethyl-cyclopentadienyl, ethyl-cyclopentadienyl, n-butyl-cyclopentadienyl, n-octyl-cyclopentadienyl, β-phenylpropyl-cyclopentadienyl, tetrahydroindenyl, propyl-cyclopentadienyl, t-butyl-cyclopentadienyl, benzyl-cyclopentadienyl, diphenylmethyl-cyclopentadienyl, trimethylgermyl-cyclopentadienyl, trimethylstannyl-cyclopentadienyl, trifluoromethyl-cyclopentadienyl, trimethylsilyl-cyclopentadienyl, pentamethylcyclopentadienyl, fluorenyl, tetrahydro- or octahydrofluorenyl, fluorenyls and indenyls which are benzo-annulated on the six-membered ring, N,N-dimethylamino-cyclopentadienyl, dimethylphosphino-cyclopentadienyl, methoxy-cyclopentadienyl dimethylboranyl-cyclopentadienyl and (N,N-dimethylantinomethyl)-cyclopentadienyl.

In addition to the first donor-acceptor bond between D and A which is obligatorily present, further donor-acceptor bonds can be formed if additional D and/or A entities are present as substituents or as parts of the respective π system. All the donor-acceptor bonds are characterised by their reversibility, as explained above. D or A independently of each other, can be situated on the metal-bonded π system or on a condensed-on ring or in a condensed-on ring or in another substituent of πI or πII. If a plurality of D or A entities is present, these can assume positions different to those cited above. The present invention accordingly comprises both the bridged molecular states (Ia) and the unbridged states (Ib). The number of D groups can be the same as or different from the number of A groups. Preferably, only one D/A bridge is present.

In addition to the D/A bridges according to the invention, covalent bridges can also be present. In this situation the D/A bridges increase the stereorigidity and the thermal stability of the catalyst. By alternating between a closed and an open D/A bond. sequential polymers of higher and lower stereoregularity can be obtained. Sequences such as these can have different chemical compositions in copolymers.

Suitable donor groups are mainly those in which the donor atom D is an element of main groups 5, 6 or 7 of the periodic table (Mendeleev) and comprises at least one free electron pair, wherein for elements of main group 5 the donor atom is in a state of bonding with substituents, and for elements of main group 6 the donor atom is in a state of bonding such as this. Donor atoms of main group 7 do not bear substituents. This is clarified below, using phosphorus P, oxygen O and chlorine Cl as examples of donor atoms, wherein "Subst." denotes said substituents and "–πI" denotes the bond to the π system, a line with an arrow has the meaning of a coordinate bonds as given in formula (I) and other lines denote electron pairs which are present:

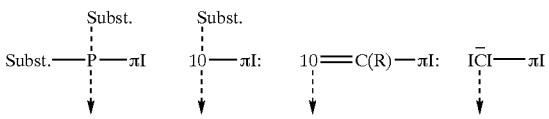

The groups which are mainly suitable as acceptor groups are those in which the acceptor atom A is an element of main group 3 of the periodic table of the elements (Mendeleev), such as boron aluminium, gallium, indium or thallium, is in a state of bonding with substituents, and comprises an electron vacancy.

D and A are linked by a coordinate bond, which is also termed a dative bond, wherein D assumes a positive (partial) charge and A assumes a negative (partial) charge.

Accordingly, a distinction is made between the donor atom D and the donor group or between the acceptor atom A and the acceptor group. The coordinate bond D→A is formed between the donor atom D and the acceptor atom A. The expression "donor group" means the unit comprising the donor atom D, the substituents which are optionally present and the electron pairs which are present: correspondingly, "acceptor group" means the unit comprising the acceptor atom A the substituents which are optionally present and the electron vacancy which is present.

The bond between the donor atom or the acceptor atom of the D or A substituent and the ring system can be interrupted by spacer groups in the sense of D-spacer-πI or A-spacer-πII. In the third of the above examples of formulae, =C(R)— represents a spacer such as this between O and πI. Examples of other spacer groups include:

dimethylsilyl,
diethylsilyl,
di-n-propylsilyl,
diisopropylsilyl,
di-n-butylsilyl,
di-t-butylsilyl,
di-n-hexylsilyl,
methylphenylsilyl,
ethylmethylsilyl,
diphenylsilyl
di(p-t-butylphenethylsilyl),
n-hexylmethylsilyl
cyclopentamethylenesilyl,
cyclotetramethylenesilyl,
cyclotrimethylenesilyl,
dimethylgermanyl,
diethylgermanyl,
phenylamino,
t-butyl amino,
methylamino,
t-butylphosphino,
ethylphosphino,
phenylphosphino,
methylene,
dimethylmethylene (i-propylidene),
diethylmethylene,
ethylene,
dimethylethylene,
diethylethylene,
dipropylethylene,
propylene,
dimethylpropylene,
diethylpropylene,
1,1-dimethyl-3-3-dimethylpropylene,
tetramethyldisiloxane
1,1,4,4-tetramethyldisilylethylene,
diphenylmethylene.

D or A are preferably bonded to the respective π system without spacer groups.

D and A, independently of each other, can be situated on the cyclopentadienyl ring or on a condensed-on benzene ring or on another substituent of πI and πII, respectively. If a plurality of D or A entities is present, they can assume various of the cited positions.

Examples of substituents on the donor atoms N, P, As, Sb, Bi, O, S, Se or Te and on the acceptor atoms B, Al, Ga, In or Tl include: $C_1$–$C_{12}$(cyclo)alkyl, such as methyl, ethyl, propyl, i-propyl, cyclopropyl, butyl, i-butyl, tert.-butyl, cyclobutyl, pentyl, neopentyl, cyclopentyl, hexyl, cyclohexyl, isomeric heptyl, octyl, nonyl, decyl and undecyl groups, and dodecyl; the $C_1$–$C_{12}$ alkoxy groups which correspond thereto; vinyl, butenyl, allyl; $C_6$–$C_{12}$ aryl, such as phenyl, naphthyl or biphenylyl, or benzyl, which can be substituted by halogens, by 1 or 2 $C_1$–$C_4$ alkyl groups, by $C_1$–$C_4$ alkoxy groups, by sulphonate, nitro or halogenoalkyl groups, or by $C_1$–$C_6$ alkyl-carboxy, $C_1$–$C_6$ alkyl-carbonyl or cyano (e.g. perfluorophenyl, m,m'-bis(trifluoromethyl)-phenyl, tri($C_1$–$C_{20}$ alkyl)silyl, tri($C_6$–$C_{12}$ aryl)silyl and analogous substituents familiar to one skilled in the art); analogous aryloxy groups: indenyl; halogens such as F, Cl, Br and I, 1-thienyl, disubstituted amino, such as ($C_1$–$C_{12}$ alkyl)$_2$amino, diphenylamino, tris-($C_1$–$C_{12}$ alkyl)-silyl, $NaSO_3$-aryl, such as $NaSO_3$-phenyl and $NaSO_3$-tolyl, $C_6H_5$—C≡C—; aliphatic and aromatic $C_1$–$C_{20}$ silyl, the alkyl substituents of which, in addition to those cited above, may comprise octyl, decyl, dodecyl, stearyl or eicosyl, and the aryl substituents of which may comprise phenyl, tolyl, xylyl, naphthyl or biphenylyl; and substituted silyl groups which are bonded to the donor or acceptor atom via —$CH_2$—, for example ($CH_3)_3SiCH_2$—, ($C_1$–$C_{12}$ alkyl)(phenyl)amino, ($C_1$–$C_{12}$ alkyl)(naphthyl)amino, ($C_1$–$C_{12}$ alkylphenyl)$_2$amino, $C_6$–$C_{12}$ aryloxy comprising the aforementioned aryl groups, $C_1$–$C_8$ perfluoroalkyl and perfluorophenyl. The preferred substituents are: $C_1$–$C_6$ alkyl, $C_5$–$C_6$ cycloalkyl, phenyl, tolyl, $C_1$–$C_6$ alkoxy, $C_6$–$C_{12}$ aryloxy, vinyl, allyl, benzyl, perfluorophenyl, F, Cl, Br, di-($C_1$–$C_6$ alkyl)-amino and diphenylamino.

Donor groups are those in which the free electron pair is located on the N, P, As, Sb, Bi, O, S, Se, Te, F, Cl, Br or I; of the latter, N, P, O and S are preferred. Examples of donor groups include: $(CH_3)_2N$—, $(C_2H_5)_2N$—, $(C_3H_7)_2N$—, $(C_4H_9)_2N$—, $(C_6H_5)_2N$—, $(CH_3)_2P$—, $(C_2H_5)_2P$—, $(C_3H_7)_2P$—, (i-$C_3H_7)_2P$—, $(C_4H_9)_2P$—, (t-$C_4H_9)_2P$—cyclohexyl$_2$P—, $(C_6H_5)_2P$—, $(CH_3)(C_6H_5)P$—, $(CH_3O)_2P$—, $(C_2H_5O)_2P$—, $(C_6H_5O)_2P$—, ($CH_3$–$C_6H_4$—O)$_2P$—, (($CH_3)_2N)_2P$—, phosphino groups which contain methyl, $CH_3O$—, $CH_3S$—, $C_6H_5S$—, —C($C_6H_5$)=O, —C($CH_3$)=O, —OSi($CH_3)_3$ and —OSi($CH_3)_2$-t-butyl, in which N and P each comprise one free electron pair and O and S each comprise two free electron pairs, and wherein in the two last-mentioned examples the doubly bonded oxygen is bonded via a spacer group, as well as systems such as the pyrrolidone ring, wherein the different ring members likewise act as spacers.

Acceptor groups are those in which an electron pair vacancy is present on the B, Al, Ga, In or Tl, preferably B, Al, Ga. In most preferably B, Al or Ga examples include: $(CH_3)_2B$—, $(C_2H_5)_2B$—, $H_2B$—, $(C_6H_5)_2B$—, $(CH_3)(C_6H_5)B$—, (vinyl)$_2B$—, (benzyl)$_2B$—, $Cl_2B$—$(CH_3O)_2B$—, $Ci_2Al$—, $(CH_3)_2Al$—, (i-$C_4H_9)_2Al$—, (Cl)($C_2H_5$)Al—, $(CH_3)_2Ga$—, $(C_3H_7)_2Ga$—, (($CH_3)_3Si$—$CH_2)_2Ga$—, (vinyl)$_2Ga$—, $(C_6H_5)_2Ga$—, $(CH_3)_2In$—, (($CH_3)_3$—$SiCH_2)_2In$— and (cyclopentadienyl)$_2In$—.

Suitable donor and acceptor groups also comprise those which contain chiral centres. Other suitable donor and acceptor groups are those in which both substituents jointly form a ring with the D or A atom. Examples thereof include

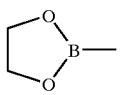 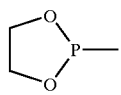

According to the invention, one or both π systems πI or πII can exist as heterocycles in the form of the aforementioned ring systems (a) to (r). In this situation, D is preferably an element of main groups 5 or 6 of the periodic table of the elements (Mendeleev); A is preferably boron here. Specific examples of hetero π systems such as these, particularly heterocycles, include:

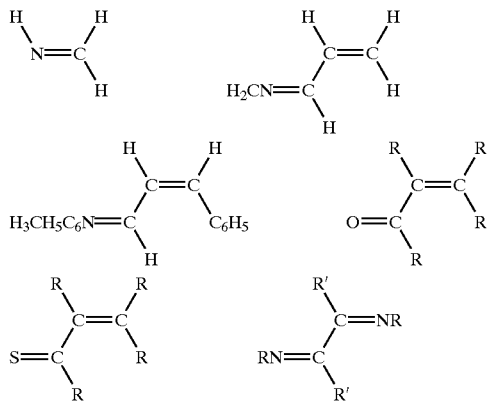

wherein

R, R'=H, alkyl, aryl or alkaryl, e.g., methyl, ethyl, t-butyl, phenyl, o,o'-di-(i-propyl)-phenyl.

Examples of heterocycles include: pyrrolyl, methylpyrrolyl, dimethylpyrrolyl, trimethylpyrrolyl, tetramethylpyrrolyl, t-butylpyrrolyl, di-t-butylpyrrolyl, indolyl, methylindolyl, dimethylindolyl, t-butylindolyl, di-t-butylindolyl, tetramethylphospholyl, tetraphenylphospholyl, triphenylphospholyl, trimethylphospholyl, phosphaindenyl, dibenzophospholyl(phosphafluorenyl) and dibenzopyrrolyl.

Examples of preferred donor-acceptor bridges between πI and πII include the following:

N→B, N→Al, P→B, P→Al, O→B, O→Al, Cl→B, Cl→Al, C=O→B, C=O→Al, wherein both atoms of these donor-acceptor bridges can be part of a hetero π system, or wherein one (donor or acceptor) atom is part of a π system and the other is a substituent of the second π system, or wherein both atoms are substituents of their respective ring and one of the rings additionally contains a hetero atom.

In accordance with the explanation given above, the two ligand systems πI and πII can be linked by one, two or three donor-acceptor bridges. This is possible because according to the invention formula (Ia) contains the D→A bridge explained above. but the ligand systems πI and πII can also comprise further D and A entities as substituents or hetero π-centres. The number of additional D→A bridges which result therefrom is zero, one or two. The number of D or A substituents on πI and πII, respectively, can be the same or different. The two ligand systems πI and πII may be covalently bridged in addition (the spacer groups described in detail above are examples of covalent bridges). Compounds without a covalent bridge are preferred. however, in which πI and πII are accordingly linked via a donor-acceptor bridge only.

M represents a transition metal of subgroups 3, 4, 5 or 6 of the periodic table of the elements (Mendeleev), including the lanthanides and actinides: examples thereof include Sc, Y, La, Sm, Nd, Lu, Ti, Zr, Hf, Th, V, Nb, Ta and Cr, Ti, Zr, Hi, V, Nb and Ta are preferred.

On the formation of the π-complex compounds according to the invention, particularly those with a metallocene structure, each positive charge of the transition metal M is compensated for by a π system in each case, particularly by a carbanion which contains a cyclopentadienyl group.

Any remaining positive charges on the central atom M are neutralised by other anions X, which are generally monovalent, two identical or different anions of which can also be linked to each other

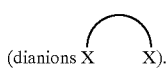

Examples thereof include monovalent or negative radicals from identical different, linear or branched, saturated or unsaturated hydrocarbons, amines, phosphines, thio alcohols, alcohols or phenols, Simple anions such as $CR_3^-$, $NR_2^-$, $PR_2^-$, $OR^-$, $SR^-$, etc., can be bonded by saturated or unsaturated hydrocarbon or silane bridges, whereupon dianions are formed and the number of bridging atoms can be 0, 1, 2, 3, 4, 5 or 6, 0 to 4 bridging atoms are preferred, and 1 or 2 bridging atoms are particularly preferred. Apart from H atoms, the bridging atoms may also bear further hydrocarbon substituents R. Examples of bridges between simple anions include —$CH_2$—, —$CH_2CH_2$—, —$(CH_2)_3$—, —CH=CH—, —$(CH=CH)_2$—, —CH=CH—$CH_2$—, —$CH_2$—CH=CH—$CH_2$—, —$Si(CH_3)_2$— and —$C(CH_3)_2$—. Examples of X include hydride, chloride, methyl, ethyl phenyl, allyl benzyl, cyclopentadienyl, fluoride, bromide, iodide, the n-propyl radical, the i-propyl radical, the n-butyl radical, the amyl radical, the i-amyl radical, the hexyl radical, the i-butyl radical, the heptyl radical, the octyl radical, the nonyl radical, the decyl radical, the cetyl radical, methoxy, ethoxy, propoxy, butoxy, phenoxy, the analogous, S-based thioalcoholates, dimethylamino, diethylamino, methylethylamino, di-t-butylamino, diphenylamino, diphenylphosphino, dicyclohexylphosphino, dimethylphosphino, methylene, ethylidene, propylidene, butadienediyl, and the ethylene glycol dianion. Examples of dianions include 1,4-diphenyl-1,3-butadiendiyl, 3-methyl-1,3-pentadiendiyl, 1,4-dibenzyl-1,3-butadienediyl, 2,4-hexadiendiyl, 1,3-pentadiendiyl, 1,4-ditolyl-1,3-butandienediyl, 1,4-bis(trimethylsilyl)-1,3-butadienediyl, and 1,3-butadiendiyl. Other examples of dianions are those which comprise hetero atoms, for instance those of structure

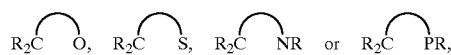

wherein the bridge has the meaning given above, 1,4-diphenyl-1,3-butadienediyl, 1,3-pentadienediyl, 1,4-dibenzyl-1,3-butadienediyl, 2,4-hexadienediyl, 3-methyl-1,3-pentadienediyl, 1,4-ditolyl-1,3-butadienediyl and 1,4-bis(trimethylsilyl)-1,3-butadienediyl are particularly preferred. Furthermore, weakly coordinating or non-coordinating anions of the aforementioned type are particularly preferred for charge compensation.

Activation through voluminous anions such as these is achieved by the reaction of D/A π -complex compounds, particularly D/A-metallocenes, with tris-(pentafluorophenyl)-borane, triphenylborane, triphenylaluminium, trityl-tetrakis-(pentafluorophenyl)-borate or N,N-dialkyl-phenyl-ammonium tetrakis-(pentafluorophenyl)borate or with the corresponding phosphonium or sulphonium salts of borates or with alkali, alkaline earth, thallium or silver salts of borates, carboranes, tosylates, triflates, perfluorocarboxylates such as trifluoroacetate, or with the corresponding acids, D/A-metallocenes in which at least one anion equivalent X constitutes alkyl, aryl or benzyl groups are preferably used here. Derivatives such as these can also be produced "in situ" by the prior reaction of D/A π-complex compounds, particularly D/A metallocenes comprising other anion equivalents such as X=F, Cl, Br, OR $NR_2$, etc, with aluminium alkyls, organolithium compounds, Mg Grignard compounds or zinc or lead alkyls. The reaction products which can be obtained therefrom can be activated, without prior isolation, with the aforementioned boranes or borates.

Depending on the charge on M, the suffix n assumes the value zero, one, two, three or four, preferably zero, one or two. In particular, and depending on which subgroup they belong to, the aforementioned subgroup metals can assume valencies or charges from two to six, preferably two to four, two of which are usually compensated by the carbanions of the metallocene compound. In the case of $Ti^{3-}$ or $La^{3-}$, the suffix n assumes a value of one, and in the case of $Zr^{4+}$ it assumes a value of two: for $Ti^{2+}$ or $Sm^{2-}$ n becomes zero In the method of preparing π-complex compounds, particularly metallocene compounds of formula (I), a reaction can be effected either between a compound each of formulae (II) and (III) given above, or between a compound each of formulae (IV) and (V) given above, or between a compound each of formulae (VI) and (VII) given above, or between a compound each of formulae (VIII) and (III) given above or between a compound each of formulae (IV) and (IX) given above, or between a compound each of formulae (X) and (VII) given above, with the separation or splitting-off of alkali metal-X, alkaline earth metal-$X_2$, silyl-X, germyl-X, stannyl-X or HX compounds in an aprotic solvent at temperatures from −78° C. to +120° C., preferably from −40° C. to +70° C., and at a molar ratio of (II):(III) or (IV):(V) or (VI):(VII) or (VIII):(III) or (IV):(IX) or (X):(VII) of 1:0.5–2, preferably 1:0.8–1.2, most preferably 1:1. In situations comprising the reaction of (VIII) with (III) or (IV) with (IX) or (X) with (VII), it is possible to dispense with an aprotic solvent if (VIII), (IX) or (X) is liquid under the reaction conditions. Examples of separated or split-off compounds such as these include: TlCl, LiCl, LiBr, LiF, LiI, NaCl, NaBr, KCl, KF, $MgCl_2$, $MgBr_2$), $CaCl_2$, $CaF_2$, trimethylchlorosilane, triethylchlorosilane, tri-(n-butyl)chlorosilane, triphenylchlorosilane, trimethylchlorogermane, trimethylchlorostannane, di-methylamine, diethylamine, dibutylamine and other compounds which can be identified by one skilled in the art from the aforementioned pattern of substitution.

Compounds of formulae (II) or (IV) are thus preferably composed of aromatic anions with a cyclopentadienyl skeleton or a heterocyclic skeleton, which contain 1 to 3 donor groups as substituents which are employed for the formation of D/A bridges and which are covalently bonded or are incorporated as members of heterocyclic rings, wherein according to the invention at least one aromatic anion constitutes a heterocyclic skeleton such as this, and said compounds comprise a cation as a counterion for the negative charge of the cyclopentadienyl skeleton. Compounds of formula (VIII) are uncharged cyclic skeletons which also comprise 1 to 3 donor groups which are used for the D/A bridge bond, but which have detachable groups $E(R^1R^2R^3)$ which are easily separable, such as silyl, germyl or stannyl groups or hydrogen, instead of ionic groups.

The second component for the formation of metallocene compounds, namely the compound of formulae (III) or (V), is likewise composed of an aromatic anion, which is identical to the cyclic skeleton of compound (II) or (IV) or is different therefrom, but which instead of donor groups bears 1 to 3 acceptor groups for the D/A bridge bond. which are incorporated either as substituents or as hetero atoms. In a corresponding manner, compounds of formula (IX) are uncharged skeletons which comprise 1 to 3 acceptor groups which are used for the D/A bridge bond and which also comprise detachable groups $F(R^4R^5R^6)$ which are easily separable.

In a completely analogous manner, compounds of formulae (VI) or (X) constitute starting materials with a preformed D→A bond, are anion-countercation compounds or uncharged skeletons with a total of 1 to 3 possible D→A bonds, and form metallocene compounds (I) by reaction with compounds of formula (VII).

The two starting materials for the method of production, namely (II) and (III) or (IV) and (V) or (VI) and (VII) or (VIII) and (III) or (IV) and (IX) or (X) and (VII), react spontaneously when placed in contact, with the simultaneous formation of the donor-acceptor-group -D→A- or with complexing of the metal cation M with the separation of $M^1X$ or $E(R^1R^2R^3)X$ or $F(R^4R^5R^6)X$ or HX. In the illustration of the donor-acceptor-group, the substituents on D and A have been omitted for the sake of clarity.

M' is a cation equivalent of an alkali or alkaline earth metal, such as Li, Na, K, ½Mg, ½Ca, ½Sr, ½Ba, or thallium.

The solvents for the method of production are aprotic, polar or nonpolar solvents such as aliphatic and aromatic hydrocarbons or aliphatic and aromatic halogenated hydrocarbons, and ethers including cyclic ethers. In principle, other aprotic solvents, such as those known to one skilled in the art, are also suitable, but those with boiling points which are too high are less preferred in the interest of simplicity of work-up. Examples of suitable solvents include n-hexane, cyclohexane, pentane, heptane, petroleum ether, toluene, benzene, chlorobenzene, methylene chloride, diethyl ether, tetrahydrofuran and ethylene glycol dimethyl ether.

The starting materials of formulae (II), (III), (IV) and (V) for the method of production can be prepared by methods known from the literature or analogously thereto. Thus, for example, by employing a procedure analogous to that described in J. of Organometallic Chem. (1971), 29, 227, commercially available trimethylsilyl-cyclopentadiene can be reacted firstly with butyllithium and then with trimethylsilyl chloride to form bis(trimethylsilyl)-cyclopentadiene The latter can in turn be reacted with boron trichloride to form trimethylsilyl-cyclopentadienyl-dichloroborane (analogously to J. of Organometallic Chem. (1979), 169, 327), which can finally be reacted with titanium tetrachloride, analogously to the procedure described in J. of Organometallic Chem. (1979), 169, 373 to form dichloroboryl-cyclopentadienyl-titanium trichloride. The last-mentioned compound already constitutes a prototype of compounds of formula (III), and furthermore can undergo a selective reaction with trimethylaluminium, whereupon the two chlorine atoms bonded to the boron atom are replaced by methyl groups and whereupon a further compound of formula (III) is formed. Under process conditions analogous to those described in J. Amer. Chem. Soc. (1983) 105 3882 and Organometallics (1982) I, 1591, commercially available cyclopentadienyl-thallium can be reacted with chlorodiphenylphosphine and can be further reacted with butyllithium, whereupon a prototype of compounds of formula (II) is obtained.

As a further example mention should be made of the formation of dimethylstannyl-diphenylphosphine-indene, by the reaction of indene firstly with butyllithium as cited above and subsequently with chlorodiphenylphosphine. Further reaction, firstly with butyllithium again and then with chlorotributyltin, results in the aforementioned compound, which after further reaction with zirconium tetrachloride yields diphenylphosphino-indenyl-zirconium trichloride as a representative of compounds of formula (IV). Syntheses and methods of preparation such as these are familiar to one skilled in the art in the field of organometallic and organoelemental chemistry, and have been published in numerous literature references, only some of which are listed above by way of example.

The Examples which are described in detail below show how heterocyclic precursors or catalysts according to the invention can be obtained. Thus pyrrolyl-lithium (formula II) can be produced from pyrrole by reaction with butyllithium, as described in J. Amer. Chem. Soc. (1982), 104, 2031, for instance. Trimethylstannyl-phosphol (formula VIII) is obtained by the reaction of 1-phenylphosphol with lithium followed by aluminium trichloride, whereupon phospholyl-lithium (formula II) is produced, which in turn reacts further with trimethylchlorostannane to form trimethylstannyl-phosphol; see J. Chem. Soc. Chem. Comm. (1988), 770. This compound can be reacted with titanium tetrachloride to form phospholyl-titanium trichloride (formula IV).

The π-complex compounds according to the invention, particularly the metallocene compounds, are outstandingly suitable as catalysts in processes for the homo- and copolymerisation of one or more $C_2$–$C_{40}$ olefines, or for the copolymerisation of one or more $C_2$–$C_{40}$ olefines with one or more $C_4$–$C_8$ isoolefines, $C_2$–$C_8$ alkynes or $C_4$–$C_8$ diolefines, in a gaseous, solution, bulk, high-pressure or slurry phase at −60 to +250° C. and at a pressure of 0.5 to 5000 bar, wherein the polymerisation can be conducted in the presence or absence of linear or branched, saturated, aromatic or alkyl-substituted aromatic $C_1$–$C_{20}$ hydrocarbons or of saturated or aromatic $C_2$–$C_{10}$ halogenated hydrocarbons. Polymerisation processes such as these can be conducted batch-wise but are preferably conducted continuously, $10^1$ to $10^{12}$ moles of (co)monomers are reacted per mole of metallocene compounds. The π-complex compounds according to the invention, particularly the metallocene compounds, can be used together with co-catalysts. The quantitative ratio of π-complex compound to co-catalyst ranges from 1 to 100,000 moles of co-catalyst per mole of π-complex. Aluminoxane compounds are examples of co-catalysts. These should be understood to include those of formula

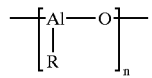

(XIII)

wherein

R represents a $C_1$–$C_{20}$ alkyl a $C_6$–$C_{12}$ aryl or benzyl, and n denotes a number from 2 to 50, preferably 10 to 35.

It is also possible to use a mixture of different aluminoxanes or a mixture of precursors thereof (aluminium alkyls or alkylaluminium halides) in combination with water (in gaseous, liquid or solid form, or in bound form, as water of crystallisation for instance) Water can also be introduced as residual moisture of the polymerisation medium, of the monomer or of a support such as silica gel.

The bonds which protrude from the square brackets of formula (XII) contain R groups or $AlR_2$ groups as terminal groups of the oligomeric aluminoxane. Aluminoxanes such as these generally exist as a mixture of a plurality thereof which have different chain lengths. Detailed research has also resulted in aluminoxanes with a ring-like or cage-like structure. The latter are preferred Aluminoxanes are commercially available compounds. In the particular case when R=$CH_3$, they are referred to as methylaluminoxanes (MAOs).

Other co-catalysts include aluminium alkyls, lithium alkyls or organo-Mg compounds such as Grignard compounds, or partially hydrolysed organoboron compounds. The preferred co-catalysts are aluminoxanes.

Activation with the co-catalyst, or the production of the voluminous, non-coordinating or weakly coordinating anion, can be effected in an autoclave or in a separate reaction vessel (pre-formation). Activation can be effected in the presence or absence of the monomer or monomers to be polymerised. Activation can be effected in an aliphatic, aromatic or halogenated solution or suspension medium or on the surface of a catalyst support material.

The π-complex compounds and the co-catalysts can either be used as such in homogeneous or heterogeneous form, or can also be used, individually or jointly, in heterogeneous form on supports. The support material here can be of an inorganic or organic nature, such as silica gel, $Al_2O_3$, $MgCl_2$, cellulose derivatives, starch and polymers. Either the π-complex compound can first be deposited on the support, or the co-catalyst, e.g. the aluminoxane and/or aluminium alkyl, can first be deposited on the support, and the other component(s) in each case can be added thereafter. In a similar manner, however, the π-complex compound in homogeneous or heterogeneous form can be activated with the co-catalyst and the activated π-complex compound can be deposited on the support thereafter.

The support materials are preferably subjected to thermal and/or chemical pretreatment in order to set the water content or the OH group concentration to a defined value or to keep these values as low as possible. Chemical pretreatment may comprise the reaction of the support with an aluminium alkyl, for example. Inorganic supports are usually heated to 100° C. to 1000° C. for 1 to 100 hours before use. The specific surface of inorganic supports such as these, particularly of silica ($SiO_2$), is between 10 and 1000 $m^2/g$, and is preferably between 100 and 800 $m^2/g$. The particle diameter is between 0.1 and 500 micrometres ($\mu$), preferably between 10 and 200$\mu$.

Examples of olefines, i-olefines, alkynes and diolefines which can be reacted by homo- or copolymerisation include ethylene, propylene, butene-1, i-butene, pentene-1, hexene-1, octene-1, 3-methyl-butene-1, 4-methyl-pentene-1, 4-methyl-hexene-1, 1,3-butadiene, isoprene, 4-methyl-1,3-pentadiene, 1,4-hexadiene, 1,5-hexadiene and 1,6-octadiene, chloroprene, acetylene and methylacetylene. With α,ω-diolefines, cyclisation polymerisation can be effected in addition, wherein poly-(methylene-1,3-cyclopentane) can be formed from 1,5-hexadiene for example:

If trialkylsilyl-substituted, αω-diolefines are used in this context, a functional group can subsequently be introduced by a reaction analogous to polymerisation. Moreover, olefines and diolefines such as these can be substituted, for example with phenyl, substituted phenyl, halogens, an esterified carboxyl group or an acid anhydride group. Examples of compounds of this type include styrene, o-, m- and p-methylstyrene, 2,4-, 2,5-, 3,4- and 3,5-dimethylstyrene, m- and p-ethylstyrene, p-tert-butyl styrene, m- and p-divinylbenzene, trivinylbenzene, o-, m- and p-chlorostyrene, o-, m- and p-bromostyrene, o-, m- and p-fluorostyrene, o-methyl-p-fluorostyrene, o-, m- and p-methoxystyrene, o-, m- and p-ethoxystyrene, indene, 4-vinyl-biphenyl, vinyl-fluorene, vinyl-anthracene, methyl methacrylate, ethyl acrylate, vinylsilane, trimethylallylsilane, vinyl chloride, vinylidene chloride, tetrafluoroethylene, isobutylene, vinyl carbazole, vinyl pyrrolidone, acrylonitrile, vinyl ethers and vinyl esters. Furthermore, ring-opening addition polymerisation is possible according to the invention, for instance of lactones such as ε-caprolactone or δ-valerolactone, or of lactams such as ε-caprolactam. The preferred monomers are: ethylene, propylene, butene, hexene, octene, 1,3-butadiene, isoprene, 1,5-hexadiene, 1,6-octadiene, styrene and the aforementioned p-substituted styrenes, methyl methacrylate, ε-caprolactone, δ-valerolactone and acetylene. The preferred copolymers are produced from the following monomer systems: ethylene/styrene, ethylene/butadiene, butadiene/styrene, isoprene/styrene, 4-methyl-1,3-pentadiene/styrene, styrene/substituted styrene, maleinimide/styrene and acrylonitrile/styrene. The possibility of producing highly syndiotactic polystyrenes is of great importance These have a degree of syndiotacticity such that the content of racemic diadene is at least 75%, preferably at least 85%, and the content of racemic pentadene is at least 30%, preferably at least 50%. The possibility of producing pure poly-(1,3-dienes) is also important, particularly those which comprise a high degree of 1,3-cis-linking. Other important poly-(1,3-dienes) are those which comprise 1,2-linking, and which accordingly give rise to unsaturated side chains.

It is possible to conduct the aforementioned (co) polymerisation processes in the presence of hydrogen, in order to adjust the molecular weights or to increase the activity, for instance.

The homo- or copolymerisation or addition polymerisation processes which can be effected with the π-complex compounds according to the invention, particularly with metallocene compounds, are conducted within the range from −60 to +250° C., preferably 50 to 200° C. and at 0.5 to 5000 bar, preferably 1 to 3000 bar, either adiabatically or isothermally. These processes include high-pressure processes in autoclaves or tubular reactors, processes in solution and bulk polymerisation processes, processes conducted in a slurry phase in stirred reactors or loop-type reactors, and processes in the gas phase, wherein the pressures employed in the slurry, solution or gas phase do not exceed 65 bar. Polymerisation processes such as these can also be conducted in the presence of hydrogen. All these processes have long been known and are familiar to one skilled in the art. One advantage of the π-complex compounds according to the invention is that by selecting their substituents they can be produced either as soluble π-complex compounds which are optionally deposited on supports, or can also be produced as insoluble π-complex compounds Soluble π-complex compounds can be used for high-pressure processes and solution processes. Heterogeneous π-complex compounds can be used in the gas phase, for example.

Due to their donor-acceptor bridge, the π-complex compounds according to the invention enable a defined opening of the two cyclopentadienyl skeletons to occur in the manner of a law, wherein, apart from a high activity, a high degree of stereoselectivity, a controlled molecular weight distribution and the uniform incorporation of comonomers are ensured. As a result of this defined, jaw-like opening process, there is also space for voluminous comonomers. Moreover, a high degree of uniformity of molecular weight distribution results from the uniform, defined site of polymerisation which occurs by insertion (single site catalyst).

The D/A structure can result in the additional stabilisation of these catalysts up to high temperatures, so that these catalysts can also be used in the high temperature range from 80 to 250° C., preferably 80 to 180° C. The possible thermal dissociation of the donor-acceptor bond is reversible, and on account of this self-organisation process and self-repair mechanism results in catalyst properties of particularly high quality. Thermal dissociation makes it possible, for example, to achieve a targeted broadening of the molecular weight distribution, whereby the polymers produced are more amenable to processing. This effect is also obtained, for example, in catalysts in which πI and πII are linked by a covalent bridge and a D/A bridge. The D/A π structures according to the invention also enable polyethylene to be formed free from defects to an extent which is not possible with classical catalysts. Ethene polymers can accordingly be produced which have extraordinarily high melting temperatures which are higher than 135° C. to 160° C. for example (maximum of the DSC curve). Amongst these linear polyethylenes, those which are produced directly in the polymerisation process and which have melting temperatures of 140 to 160° C. (maxima of the DSC curve), preferably 142 to 160° C., most preferably 144 to 160° C., are particularly important. This applies in particular to those which can be produced using the claimed π-complex compounds. Compared with known polyethylenes, new high-melting polyethylenes such as these have improved mechanical properties and resistance to thermal deformation (capacity for sterilisation in medical applications), and therefore open up possibilities for the use of polyethylenes which have hitherto appeared impossible and which could only be achieved hitherto, for example, by highly tactic polypropylene. Other features include high enthalpies of fusion and high PE molecular weights.

Over a wide temperature range, the molecular weight of the PE is in fact reduced by increasing the polymerisation temperature, but this occurs without any appreciable decrease in activity and without departing as a whole from the sphere of high PE molecular weights and high PE melting temperatures which are of interest commercially.

Furthermore, it has been observed that π-complex compounds of suitable symmetry according to the invention result in the regiospecific (isotactic, syndiotactic) polymerisation of suitable monomers, but in the upper part of said temperature range initiate what is an increasingly non-specific (atactic) linking of the monomer units for the same monomer. This phenomenon is not yet completely understood, but could be in agreement with the observation that coordinate bonds on which an ionic bond is superimposed, such as the donor-acceptor bonds in π-complex compounds according to the invention, exhibit an increasing extent of reversibility at elevated temperatures. Thus it has been observed during the copolymerisation of ethylene and propylene that when both comonomers are present in the same amount a copolymer with a high propylene content is formed at a low copolymerisation temperature, whilst the propylene content decreases with increasing polymerisation temperature until finally it is polymers which predominantly contain ethylene which are formed at high temperature. The reversible dissociation and association of the D/A structure and the rotation of the π systems in relation to each other which thereby becomes possible can shown in the formula exemplified above is then the site for the insertion of an olefine for polymerisation.

Furthermore, the π-complex compounds or metallocene compounds according to the invention are suitable for the production both of thermoplastic and of elastomeric poly-

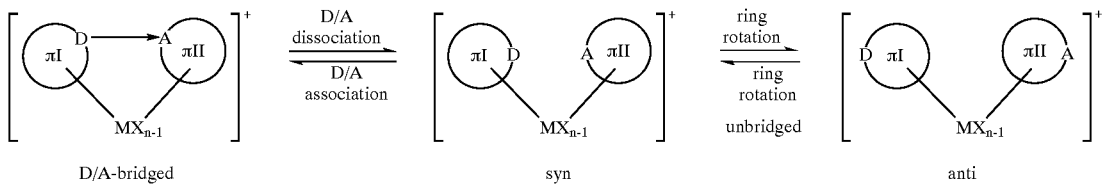

be schematically illustrated as follows:

Due to this change between a bridged and an unbridged catalyst structure, catalysts are available for the first time which are suitable for the production of stereospecific/aspecific ligand arrangements which change in a defined manner using one catalyst only under alternating conditions.

This temperature-dependent dynamic behaviour of the π-complex compounds or metallocene compounds according to the invention at different temperatures accordingly makes it possible to produce different stereo block copolymers, for instance those of the isotactic and atactic polypropylene (i-PP-a-PP)$_n$ type, which can be of different composition (a) with respect to the relative amounts of isotactic polypropylene (i-PP) and atactic polypropylene (a-PP) and (b) with respect to the block or sequence lengths.

Another valuable property of D/A π-complex compounds according to the invention is the possibility of self-activation and thus the possibility of dispensing with expensive co-catalysts, particularly in the case of dianionic

(X X)

derivatives. In this situation, in the opened form of the D/A π-complex compound, the acceptor atom A binds an X ligand,, for example one side of a dianion, with the formation of a zwitterionic π-complex structure and thus produces a positive charge on the transition metal, whilst the acceptor atom A assumes a negative charge. A self-activation process such as this can occur intramolecularly or intermolecularly. This can be illustrated by the example of the preferred linking of two X ligandis to a chelate ligand, namely that of the butadienediyl-derivative:

mers by the various methods of production cited above, wherein both highly crystalline polymers with an optimised melting range and amorphous polymers with an optimised glass transition temperature can be obtained.

EXAMPLES

All the reactions were conducted under stringently anaerobic conditions and using Schlenk techniques or high vacuum technique. The solvents used were dried and saturated with argon. Chemical shifts δ are given in ppm relative to the respective standard: $^1$H(tetramethylsilane), $^{13}$C (tetramethylsilane), 31P(85% H$_3$PO$_4$), $^{11}$B(boron trifluoride etherate; δ=−18.1 ppm). Negative algebraic signs denote a shift to the higher field.

Example 1 bis-(trimethylsilyl)-cyclopentadiene; compound 1

14.7 g (0.106 mole) trimethylsilyl-cyclopentadiene (purchased from Fluka) and 150 ml tetrahydrofuran (THF) were placed in a reaction flask and cooled to 0° C. 47.4 ml of a solution of butyllithium in n-hexane (2.3 molar; total amount 0.109 mole) were then added drop-wise thereto over 20 minutes. After the addition was complete, the yellow solution was stirred for a further hour; thereafter the cooling bath was removed. The solution was stirred for a further hour at room temperature and was thereafter cooled to −20° C. 14.8 ml (0.117 mole) trimethylsilyl chloride were then added drop-wise over 10 minutes and the reaction mixture was stirred at −10° C. for two hours. Thereafter, the cooling bath was removed and the reaction solution was heated to room temperature and was subsequently stirred for a further hour. The reaction mixture was filtered through celite the filter was washed with hexane, and the hexane was removed from the purified filtrate under vacuum. After distillation at

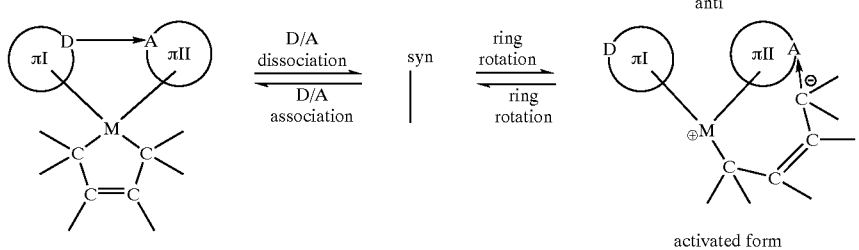

The binding site between the transition metal M and the C atom, which is still bonded, of the butadienediyl dianion 26° C. under 0.4 mbar, the crude product yielded 19 g of a pure product corresponding to compound 1 (85% of the theoretical yield). The boiling point and NMR data corresponded to the data in the literature (J. Organometallic Chem. 29 (1971), 227; ibid. 30 (1971), C 57; J. Amer. Chem. Soc. 102 (1980), 4429: J. Gen. Chem. USSR Eng. Transl. 43 (1973), 1970; J. Chem. Soc., Dalton Trans. 1980, 1156)

$^1$H NMR (400 MHz, C$_6$D$_6$): δ=6.74 (m,2H), 6.43 (m,2H), −0.04 (s.18H).

Example 2 trimethylsilyl-cyclopentadienyl-dichloroborane; compound 2

16 g (0.076 mole) of compound 1 were placed in a round bottom flask which was equipped with a dry ice cooling bath. 8.9 g (0.076 mole) BCl$_3$ were condensed at −78° C. in a Schlenk tube and thereafter were added drop-wise to the round bottom flask over a period of 5 minutes. The reaction mixture was slowly heated to room temperature over 1 hour and was then maintained at 55 to 60° C. for a further 2 hours. All the volatile compounds were removed under vacuum (3 mm Hg=4 mbar). Subsequent distillation at 39° C. and 0.012 mbar gave 14.1 g of compound 2 (85% of the theoretical yield). The $^1$H NMR results agreed with the literature data and showed that a series of isomers had been produced (see J. Organometallic Chem. 169 (1979), 327). $^{11}$B NMR (64.2 MHz, C$_6$D$_6$): δ+31.5.

Example 3 dichloroboranyl-cyclopentadienyl-titanium trichloride, compound 3

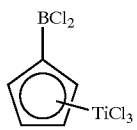

3

11.4 g (0.052 mole) of compound 2 and 100 ml methylene chloride (CH$_2$Cl$_2$) were placed in a 250 ml Schlenk tube. These solution was cooled to −78° C. and 9.8 g (5.6 ml, 0.052 mole) titanium tetrachloride were added drop-wise over 10 minutes. The red solution obtained was slowly heated to room temperature and was stirred for a further 3 hours. The solvent was removed under vacuum, whereupon a yellowish product was obtained. 200 ml hexane were added to the crude solid, and yellow solution obtained was filtered and cooled overnight in a refrigerator, whereupon 12.3 g (79% of the theoretical yield) of yellow crystals of compound 3 were obtained. It should be mentioned that in J. Organometallic Chem. 169 (1979), 373, 62% of the theoretical yield was obtained when the reaction was conducted in a hydrocarbon solvent such as petroleum ether or methylcyclohexane.

$^1$H NMR (400 MHz, CD$_2$Cl$_2$): δ=7.53 (t, J=2.6 Hz, 2H), 7.22 (t, J=2.6 Hz, 2H). $^{11}$B-NMR (64.2 MHz, CD$_2$Cl$_2$). δ=+33.

Example 4 dimethylboranyl-cyclopentadienyl titanium trichloride; compound 4

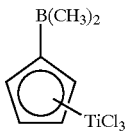

4

2.37 g (0.0079 mole) of compound 3 in 100 ml hexane were cooled to 0° C. in a round bottom flask and were treated drop-wise with 4 ml of a 2 molar solution of aluminium trimethyl in toluene (0.08 mole). After the addition was complete, the cooling bath was removed and all the volatile constituents were removed under vacuum. The remaining yellow solid was then dissolved in pentane, solid constituents were filtered off, and the clear filtrate was cooled to −78° C., whereupon 1.5 g (74% of the theoretical yield) of compound 4 were obtained. It should be remarked that in J. Organometallic Chem. 169 (1979), 373, a yield of 87% of the theoretical yield was quoted when tetramethyltin was used as the alkylating agent, it did not prove possible, however, to obtain compound 4 free from the trimethyltin chloride formed.

$^1$H NMR (400 MHz, CD$_2$Cl$_2$): δ7.48 (t, J=2.5 Hz, 2H), 7.23 (t, J=2.5 Hz, 2H), 1.17 (s, 6H). $^{11}$B NMR (64.2 MHz, CD$_2$Cl$_2$); δ=+56.

Example 5 pyrrole-lithium; compound 5

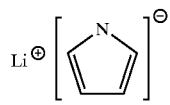

5

59 ml of a solution of butyllithium (2.5 molar in hexane, 0.148 mole) were slowly added at −20° C. to a solution of 9.9 g pyrrole (0.148 mole) in 200 ml hexane, whereupon a white solid was formed. The batch was subsequently stirred for 2 hours at room temperature and the solid was recovered by filtration, washed twice with 20 ml hexane each time, and dried under vacuum. This method gave 6 g, of compound 5(156% of the theoretical yield).

1H NMR (400 MHz, THF): δ=6.71 (s, 2H), 5.95 (s, 2H).

Example 6 dimethylboranyl-bridged cyclopentadienyl-pyrrole-titanium dichloride; compound 6

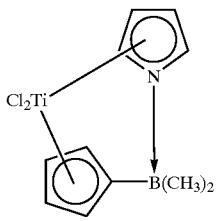

A solution of 1.34 g (0.005 mole) of compound 4 in 20 ml toluene was added to 0.38 g (0.005 mole) of compound 5 over 5 minutes at −78° C. The cooling bath was thereafter removed, and the batch was stirred for a further 2 hours at room temperature. Thereafter, the red solid which was formed was filtered off, the yellow filtrate was discarded. The red solid was washed with toluene and dried under vacuum. 1.14 g of solid product was obtained, which contained a small proportion of LiCl.

$^1$H NMR (400 MHz, THF) δ=6.89 (pseudo-t, J=2.3 Hz, 2H), 6.64 (m, 2H), 6.59 (pseudo-t J=2.35 Hz, 2H), 5.73 (pseudo-t, J=1.7 Hz, 2H), 0.06 (s, 6H). $^{11}$B NMR (80 MHz, THF) δ=−26 ppm.

Example 7 ethylene-propylene copolymerisation 10 g propene were condensed into, and 100 ml of dry toluene were introduced into a dry, oxygen-free, stirred V4A steel autoclave which had been heated under vacuum at 100° C. The batch was heated to 60° C., the pressure which was reached (5.5 bar) was increased by 2 bar with ethene (to 7.5 bar) and the catalyst was added by means of a pressure lock The D/A-metallocene catalyst (compound 6) had been preformed beforehand with MAO (methylaluminoxane: 10% in toluene, molecular weight 900 g/mole) in an Al/Ti atomic (molar) ratio of 5000:1 over 15 minutes in toluene at room temperature. The amount of catalyst used contained 1×10$^{-6}$ mole Ti and 5×10$^{-3}$ mole Al. Polymerisation was conducted, with stirring, for 30 minutes at 60 to 65° C. (exothermic). After depressurising the autoclave. the highly viscous reaction mixture was stirred into a mixture of 500 ml ethanol and 50 ml concentrated aqueous hydrochloric acid (37%). The suspension of the white polymer which was thereby precipitated was stirred for a further 17 hours and the solid was subsequently isolated by filtration, thoroughly washed with ethanol and dried at 100° C. to constant weight. The yield of EPM was 0.5 g, which corresponded to a catalyst activity of 1 tonne copolymer per mole titanium per hour. A propylene content of 25% by weight was determined by IR spectroscopy. The limiting viscosity as measured in o-dichlorobenzene at 140° C. was 1.02 dl/g. DSC measurements gave a glass transition temperature Tg=−44° C. and a vitrification temperature of −53° C. GPC measurements gave a weight average molecular weight M$_w$ of 119 kg/mole. M$_w$/M$_n$=2.62.

Example 8

1-phenyl-2,3,4,5-tetramethyl-phosphol, compound 7

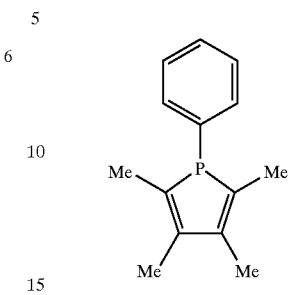

Corresponding to the procedure described in Organometallics 7 (1988), 921, a solution of 11.7 g (0.216 mole) 2-Bu-tin in 150 ml CH$_2$Cl$_2$ was slowly added to 15.3 g (0.115 mole) AlCl$_3$ in CH$_2$Cl$_2$ (0° C., 30 minutes). The batch was subsequently stirred for 45 minutes at 0° C., then the cooling bath was removed and stirring was continued for a further hour. Thereafter, the solution was cooled to −50° C. and a solution of 21.4 g (0.12 mole) phenyl-dichlorophosphine in CH$_2$Cl$_2$ was added over 20 The cooling bath was thereafter removed, and the dark red solution was stirred for a further one hour and was then added at −30° C. to a solution of 27 g (0.13 mole) tributylphosphine in 100 ml CH$_2$Cl$_2$. The redcolour disappeared immediately, leaving a yellow solution. After the addition was complete, the solvent was removed under vacuum, a thick yellow oil remained. The oil was taken up in hexane and was washed with saturated aqueous NaHCO$_3$ solution and H$_2$O under an Ar atmosphere. After drying over MgSO$_4$, the hexane was removed under vacuum, 18.2 g product remained as a clear oil (yield 78%) $^1$H NMR (400 MHz, CDCl$_3$) δ: 7.3 (m, 5H), 2.0 (m, 12H) $^{31}$P NMR (161.9 MHz, CDCl$_3$) δ:16.8 ppm.

Example 9 lithium-2,3,4,5-tetramethyl-phosphol; compound 8

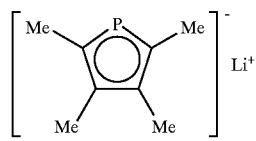

Corresponding to the procedure described in Organometallics 7 (1988), 921, 0.52 g (0.074 mole) lithium was added to a solution of 7 g (0.032 mole) of compound 7 in 150 ml tetrahydrofuran (THF) and was stirred overnight. The red solution obtained was filtered through a frit to remove residual solids and the filtrate was cooled to 0° C. Thereafter, a solution of 1.45 g (0.01 mole) AlCl in 20 ml THF was added drop-wise and the solution was brought to room temperature. An aliquot portion was taken for analysis and the remaining solution was used directly for the preparation of compound 9.

$^{31}$P NMR (161.9 MHz, THF) δ: 63.7 ppm.

Example 10 dimethylboranyl-cyclopentadienyl-tetramethylphospholyl-titanium dichloride; compound 9

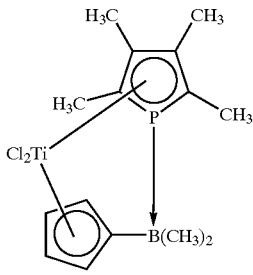

The THF solution from Example 9, which contained 1.46 g (0.01 mole) of compound 8, was introduced into a round bottom flask and the THF was removed under vacuum. After adding toluene and cooling to −78° C. a solution of 2.6 g (0.01 mole) of compound 4 in 20 ml toluene was slowly added with stirring, whereupon a red slurry was formed. After the addition was complete, the slurry was brought to room temperature and stirred for a further 1 hour After removing undissolved residual solid by filtration, the toluene was removed under vacuum. and hexane was added to the remaining oily solid. The hexane solution was likewise freed by filtration from the undissolved solid which remained. and was maintained at −20° C. overnight. After removing the hexane by decantation. 0.5 g of a green solid was obtained which was identified as compound 9 (yield 14%). $^1$H NMR (200 MHz, CD$_2$Cl$_2$). δ=6.64 (m,2H), 6.57 (m,2H), 2.11 (d, $J_{H-P}$=10 Hz, 6H); 2.09 (s,6H), 0.87 (d, $J_{H-P}$=5.3 Hz, 6H). $^{31}$P NMR (161.9 MHz, THF): δ=95.6 ppm $^{11}$B NMR (80 MHz, CD$_2$Cl$_2$): δ=39 (br, m) ppm.

The donor-acceptor bond length d(P→B) in [(Me$_4$phospholyl)BMe$_2$(cp)TiCl$_2$] (=the above compound 9) was determined as 2.11 Å by means of X-ray structural analysis (FIG. 1).

Example 11 polystyrene 78.15 g (89.8 ml) toluene (distilled over sodium) were placed in a baked-out 250 ml four-necked flask which was flushed with argon and fitted with a thermometer and an argon inlet. Thereafter. 0.5 mole (52.07 g) styrene (distilled over calcium hydride) was added. Polymerisation was initiated by the addition of the catalyst component comprising 10 mmole (6.6 ml) MAO as a 10% solution in toluene and 10 μmole [(Me$_4$phospholyl) BMe$_2$(cp)TiCl$_2$]≅3.62 mg in 4.5 ml toluene.

| Polymerisation time: | 1 hour at 25° C. and |
| --- | --- |
|  | 1 hour at 50° C. |

The suspension which was formed was precipitated in 1 liter of CH$_3$OH/HCl (90/10). the solid was filtered off and subsequently stirred for 2 hours with 1 liter of CH$_3$OH. followed by filtration and drying at 90° C. in a vacuum drying oven.

The limiting viscosity at 140° C. in orthodichlorobenzene was 0.43 dl/g. DSC measurements during the 2nd heat-up gave two fusion maxima:

$T_{m1}$ 262° C. and $T_{m2}$=268° C. (main peak).

NMR examination showed a syndiotactic polystyrene.

Example 12

Polybutadiene 81.5 g (93.67 ml) toluene which had previously been distilled over sodium were placed in a baked-out 250 ml four-necked flask which was flushed with argon and which was fitted with a thermometer, a dry ice condenser and an argon inlet, and I mole (54.1 g) 1,3-butadiene was condensed therein.

Polymerisation was initiated by the addition of the catalyst component:

10 mmole MAO=6.6 ml as a 10% solution in toluene, and

10 μmole [(Me$_4$phospholyl) BMe$_2$(cp)TiCl$_2$]≅3.34 mg in 4.5 ml toluene.

| Polymerisation time: | 1 hour at 18° C. and |
| --- | --- |
|  | 1 hour at 25° C. (heating bath 50° C.) |

The viscous solution was precipitated in 1 liter of ethanol, the solid was filtered off and subsequently stirred for 2 hours with 1 liter of ethanol, followed by filtration and drying at 90° C. in a vacuum drying oven.

Yield: 5.3 g high molecular weight polybutadiene

| Microstructure as determined by FT-IR: | 1,4-cis | 85% |
| --- | --- | --- |
|  | 1,4-trans | 1.5% |
|  | 1,2-vinyl | 13.5% |

Example 13

Polystyrene

The procedure was as in Example 11, except that the pyrrolyl catalyst from Example 6 [(pyrrolyl)BMe$_2$(cyclopentadienyl)TiCl$_2$] was used here instead of the phospholyl catalyst. A highly syndiotactic polystyrene was formed. The limiting viscosity in orthodichlorobenzene at 140° C. was 0.54 dl/g. DSC measurements during the 2nd heat-up gave Tm$_1$=264° C. and Tm$_2$=270° C. (main peak).

What is claimed is:

1. A π-complex compound comprising the formula

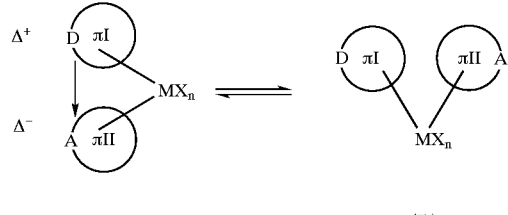

(Ia)                    (Ib)

wherein

πI and πII represent π systems which bear charges which are different from each other or which are electrically neutral, and which can be singly- or doubly-condensed with unsaturated or saturated five- or six-membered rings, D denotes a donor atom which is a substituent of πI or is part of the π system of πI, and which has at least one free electron pair available in its respective bonding state, A denotes an acceptor atom which is a substituent of πII or is part of the π system of πII, and which has an electron pair vacancy in its respective bonding state, wherein D and A are linked by a reversible coordinate bond in such a way that the donor group assumes a positive (partial) charge and the acceptor group assumes a negative (partial) charge, and wherein at least one of D and A is part of the associated π system in each case, wherein D and A themselves may comprise substituents, wherein each π system or each condensed-on ring system can contain one or more D or A entities, or D and A entities, and wherein in πI and πII, in the non-condensed or in the condensed form, one to all of the H atoms of the π system, independently of each other, can be substituted by identical or different radicals from the group comprising a linear or branched $C_1$–$C_{20}$ alkyl which can be substituted singly to completely by halogens, can be substituted singly to three-fold by phenyl or can be substituted singly to three-fold by vinyl; a $C_6$–$C_{12}$ aryl, and a halogenoaryl comprising 6 to 12 C atoms; and said H atoms can also be singly- or doubly-substituted by D and A, so that the reversible coordinate D→A bond is formed (i) between D and A, which both constitute parts of the respective π system, or (ii) from the D or A part of the π system and the other substituent of the non-condensed π system or of the condensed-on ring system in each case, or (iii) both D and A are such substituents, wherein in the case of (iii) at least one additional D or A entity or both is (are) part of the π system or of the condensed-on ring system, M represents a transition metal of subgroups III, IV, V or VI of the periodic table of the elements (Mendeleev, including the lanthanides and actinides), X denotes an anion equivalent, and n denotes the numbers zero, one, two, three or four depending on the charge of M and on those of πI and πII.

2. A method for the homo- or copolymerization of one or more olefines, i-olefines, alkynes or diolefines as monomers, or for ring-opening addition polymerization in a gaseous, solution, bulk, high-pressure or slurry phase at −60 to +250° C. and at 0.5 to 5000 bar and in the presence or absence of saturated or aromatic hydrocarbons or of saturated or aromatic halogenated hydrocarbons, wherein π-complex compounds are used as catalysts in an amount of $10^1$ to $10^{12}$ moles of monomers per mole of π-complex, said π-complex compounds comprising the formula

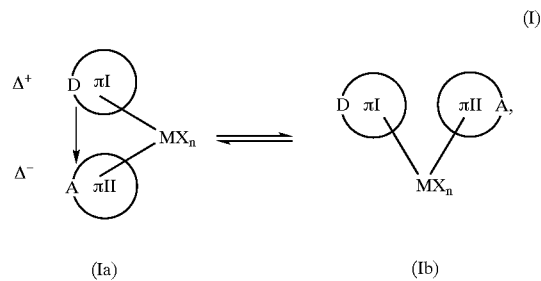

(Ia)          (Ib)

wherein

πI and πII represent π systems which bear charges which are different from each other or which are electrically neutral, and which can be singly- or doubly-condensed with unsaturated or saturated five- or six-membered rings, D denotes a donor atom which is a substituent of πI or is part of the π system of πI, and which has at least one free electron pair available in its respective bonding state, A denotes an acceptor atom which is a substituent of πII or is part of the π system of πII, and which has an electron pair vacancy in its respective bonding state, wherein D and A are linked by a reversible coordinate bond in such a way that the donor group assumes a positive (partial) charge and the acceptor group assumes a negative (partial) charge, and wherein at least one of D and A is part of the associated π system in each case, wherein D and A themselves may comprise substituents, wherein each π system or each condensed-on ring system can contain one or more D or A entities, or D and A entities, and wherein in πI and πII, in the non-condensed or in the condensed form, one to all of the H atoms of the π system, independently of each other, can be substituted by identical or different radicals from the group comprising a linear or branched $C_1$–$C_{20}$ alkyl which can be substituted singly to completely by halogens, can be substituted singly to three-fold by phenyl or can be substituted singly to three-fold by vinyl; a $C_6$–$C_{12}$ aryl, and a halogenoaryl comprising 6 to 12 C atoms; and said H atoms can also be singly- or doubly-substituted by D and A, so that the reversible coordinate D→A bond is formed (i) between D and A, which both constitute parts of the respective π system, or (ii) from the D or A part of the π system and the other substituent of the non-condensed π system or of the condensed-on ring system in each case, or (iii) both D and A are such substituents, wherein in the case of (iii) at least one additional D or A entity or both is (are) part of the π system or of the condensed-on ring system, M represents a transition metal of subgroups III, IV, V or VI of the periodic table of the elements (Mendeleev, including the lanthanides and actinides), X denotes an anion equivalent, and n denotes the numbers zero, one, two, three or four depending on the charge of M and on those of πI and πII.

3. A π-complex compound according to claim 1, wherein the πI π system is a cyclopentadienyl skeleton selected from the group consisting of cyclopentadiene, substituted cyclopentadiene, indene, substituted indene, fluorene and substituted fluorene, in which condensed-on aromatic rings can be partially or completely hydrogenated.

4. A π-complex compound according to claim 1, wherein elements from the group consisting of N, P, As, Sb, Bi, O, S, Se, Te, F, Cl, Br, I, are used as donor atoms D.

5. A π-complex compound according to claim 1, wherein elements from the group consisting of B, Al, Ga, In, Tl, are used as acceptor atoms A.

6. A π-complex compound according to claim 1, wherein donor-acceptor bridges are used from the group consisting of N→B, N→Al, P→B, P→Al, O→B, O→Al, Cl→B, Cl→Al, C=O→B, C=O→Al.

7. A π-complex compound according to claim 1, wherein M represents Sc, Y, La, Sm, Nd, Lu, Ti, Zr, Hf, Th, V, Nb, Ta or Cr.

8. A π-complex compound according to claim 1, wherein the atoms D or A is part of the ring of the associated π system.

9. A method according to claim 2, wherein the π-complex compounds are used together with an aluminoxane or with another ionizing agent as a catalyst system.

10. A reaction product of ionizing agents with π-complexes; said reaction product comprises the formula (XI)

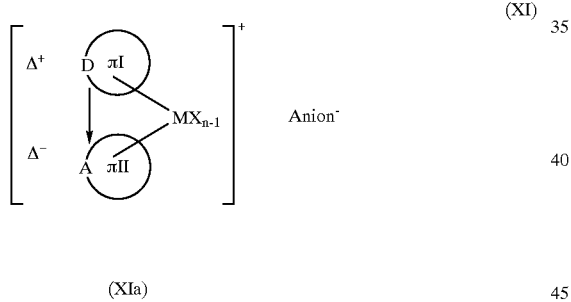

(XIa)

or

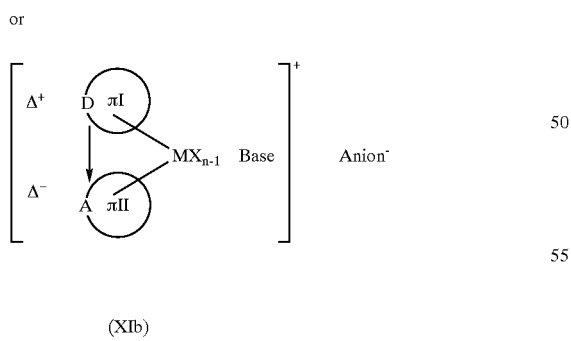

(XIb)

wherein

Anion represents the entire, bulky, poorly coordinating anion and Base represents a Lewis base; said π-complex compounds comprising the formula

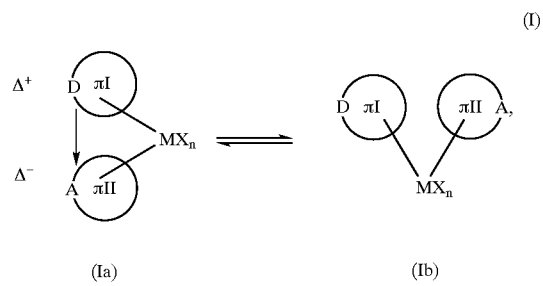

wherein

πI and πII represent π systems which bear charges which are different from each other or which are electrically neutral, and which can be singly- or doubly-condensed with unsaturated or saturated five- or six-membered rings, D denotes a donor atom which is a substituent of πI or is part of the π system of πI, and which has at least one free electron pair available in its respective bonding state, A denotes an acceptor atom which is a substituent of πII or is part of the π system of πII, and which has an electron pair vacancy in its respective bonding state, wherein D and A are linked by a reversible coordinate bond in such a way that the donor group assumes a positive (partial) charge and the acceptor group assumes a negative (partial) charge, and wherein at least one of D and A is part of the associated π system in each case, wherein D and A themselves may comprise substituents, wherein each π system or each condensed-on ring system can contain one or more D or A entities, or D and A entities, and wherein in πI and πII, in the non-condensed or in the condensed form, one to all of the H atoms of the π system, independently of each other, can be substituted by identical or different radicals from the group comprising a linear or branched $C_1$–$C_{20}$ alkyl which can be substituted singly to completely by halogens, can be substituted singly to three-fold by phenyl or can be substituted singly to three-fold by vinyl; a $C_6$–$C_{12}$ aryl, and a halogenoaryl comprising 6 to 12 C atoms; and said H atoms can also be singly- or doubly-substituted by D and A, so that the reversible coordinate D→A bond is formed (i) between D and A, which both constitute parts of the respective π system, or (ii) from the D or A part of the π system and the other substituent of the non-condensed π system or of the condensed-on ring system in each case, or (iii) both D and A are such substituents, wherein in the case of (iii) at least one additional D or A entity or both is (are) part of the π system or of the condensed-on ring system, M represents a transition metal of subgroups III, IV, V or VI of the periodic table of the elements (Mendeleev, including the lanthanides and actinides), X denotes an anion equivalent, and n denotes the numbers zero, one, two, three or four depending on the charge of M and on those of πI and πII.

11. A rearrangement product formed by self-activation of π-complex compounds wherein after the opening of the D/A bond the acceptor atom A binds an X ligand with the formation of a zwitterionic π-complex structure, wherein a positive charge is produced on the transition metal M and a negative charge is produced on the acceptor atom A, and wherein a further X ligand represents H or substituted or unsubstituted C, in the bond of which to the transition metal M an olefine is inserted for polymerization, wherein 2 X ligands are preferably linked to one chelate ligand; said π-complex compounds comprising the formula

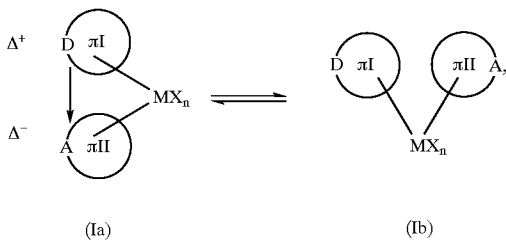

(I)

(Ia)  (Ib)

wherein

πI and πII represent π systems which bear charges which are different from each other or which are electrically neutral, and which can be singly- or doubly-condensed with unsaturated or saturated five- or six-membered rings, D denotes a donor atom which is a substituent of πI or is part of the π system of πI, and which has at least one free electron pair available in its respective bonding state, A denotes an acceptor atom which is a substituent of πII or is part of the π system of πII, and which has an electron pair vacancy in its respective bonding state, wherein D and A are linked by a reversible coordinate bond in such a way that the donor group assumes a positive (partial) charge and the acceptor group assumes a negative (partial) charge, and wherein at least one of D and A is part of the associated π system in each case, wherein D and A themselves may comprise substituents, wherein each π system or each condensed-on ring system can contain one or more D or A entities, or D and A entities, and wherein in πI and πII, in the non-condensed or in the condensed form, one to all of the H atoms of the π system, independently of each other, can be substituted by identical or different radicals from the group comprising a linear or branched $C_1$–$C_{20}$ alkyl which can be substituted singly to completely by halogens, can be substituted singly to three-fold by phenyl or can be substituted singly to three-fold by vinyl; a $C_6$–$C_{12}$ aryl, and a halogenoaryl comprising 6 to 12 C atoms; and said H atoms can also be singly- or doubly-substituted by D and A, so that the reversible coordinate D→A bond is formed (i) between D and A, which both constitute parts of the respective π system, or (ii) from the D or A part of the π system and the other substituent of the non-condensed π system or of the condensed-on ring system in each case, or (iii) both D and A are such substituents, wherein in the case of (iii) at least one additional D or A entity or both is (are) part of the π system or of the condensed-on ring system, M represents a transition metal of subgroups III, IV, V or VI of the periodic table of the elements (Mendeleev, including the lanthanides and actinides, X denotes an anion equivalent, and n denotes the numbers zero, one, two, three or four depending on the charge of M and on those of πI and πII.

12. The production of highly syndiotactic polystyrenes comprising the homo- or copolymerization of one or more olefines, i-olefines, alkynes or diolefines as monomers, or for ring-opening addition polymerization in a gaseous, solution, bulk, high-pressure or slurry phase at −60 to +250° C. and at 0.5 to 5000 bar and in the presence or absence of saturated or aromatic hydrocarbons or of saturated or aromatic halogenated hydrocarbons, wherein π-complex compounds are used as catalysts in an amount of $10^1$ to $10^{12}$ moles of monomers per mole of π-complex, said π-complex compounds comprising the formula

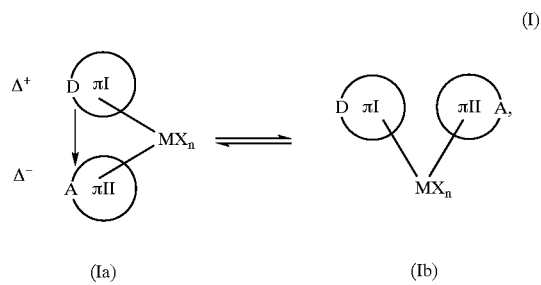

(I)

(Ia)  (Ib)

wherein

πI and πII represent π systems which bear charges which are different from each other or which are electrically neutral, and which can be singly- or doubly-condensed with unsaturated or saturated five- or six-membered rings, D denotes a donor atom which is a substituent of πI or is part of the π system of πI, and which has at least one free electron pair available in its respective bonding state, A denotes an acceptor atom which is a substituent of πII or is part of the π system of πII, and which has an electron pair vacancy in its respective bonding state, wherein D and A are linked by a reversible coordinate bond in such a way that the donor group assumes a positive (partial) charge and the acceptor group assumes a negative (partial) charge, and wherein at least one of D and A is part of the associated π system in each case, wherein D and A themselves may comprise substituents, wherein each π system or each condensed-on ring system can contain one or more D or A entities, or D and A entities, and wherein in πI and πII, in the non-condensed or in the condensed form, one to all of the H atoms of the π system, independently of each other, can be substituted by identical or different radicals from the group comprising a linear or branched $C_1$–$C_{20}$ alkyl which can be substituted singly to completely by halogens, can be substituted singly to three-fold by phenyl or can be substituted singly to three-fold by vinyl; a $C_6$–$C_{12}$ aryl, and a halogenoaryl comprising 6 to 12 C atoms; and said H atoms can also be singly- or doubly-substituted by D and A, so that the reversible coordinate D→A bond is formed (i) between D and A, which both constitute parts of the respective π system, or (ii) from the D or A part of the π system and the other substituent of the non-condensed π system or of the condensed-on ring system in each case, or (iii) both D and A are such substituents, wherein in the case of (iii) at least one additional D or A entity or both is (are) part of the π system or of the condensed-on ring system, M represents a transition metal of subgroups III, IV, V or VI of the periodic table of the elements (Mendeleev, including the lanthanides and actinides), X denotes an anion equivalent, and n denotes the numbers zero, one, two, three or four depending on the charge of M and on those of πI and πII.

13. The production of pure poly-(1,3-dienes), comprising the homo- or copolymerization of one or more olefines, i-olefines, alkynes or diolefines as monomers, or for ring-opening addition polymerization in a gaseous, solution, bulk, high-pressure or slurry phase at −60 to +250° C. and at 0.5 to 5000 bar and in the presence or absence of saturated or aromatic hydrocarbons or of saturated or aromatic halogenated hydrocarbons, wherein π-complex compounds are used as catalysts in an amount of $10^1$ to $10^{12}$ moles of monomers per mole of π-complex, said π-complex compounds comprising the formula

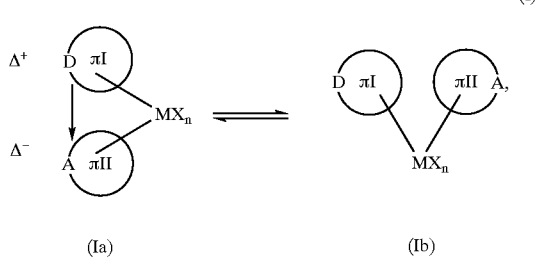

(Ia)    (Ib)    (I)

wherein

πI and πII represent π systems which bear charges which are different from each other or which are electrically neutral, and which can be singly- or doubly-condensed with unsaturated or saturated five- or six-membered rings, D denotes a donor atom which is a substituent of πI or is part of the π system of πI, and which has at least one free electron pair available in its respective bonding state, A denotes an acceptor atom which is a substituent of πII or is part of the π system of πII, and which has an electron pair vacancy in its respective bonding state, wherein D and A are linked by a reversible coordinate bond in such a way that the donor group assumes a positive (partial) charge and the acceptor group assumes a negative (partial) charge, and wherein at least one of D and A is part of the associated π system in each case, wherein D and A themselves may comprise substituents, wherein each π system or each condensed-on ring system can contain one or more D or A entities, or D and A entities, and wherein in πI and πII, in the non-condensed or in the condensed form, one to all of the H atoms of the π system, independently of each other, can be substituted by identical or different radicals from the group comprising a linear or branched $C_1$–$C_{20}$ alkyl which can be substituted singly to completely by halogens, can be substituted singly to three-fold by phenyl or can be substituted singly to three-fold by vinyl; a $C_6$–$C_{12}$ aryl, and a halogenoaryl comprising 6 to 12 C atoms; and said H atoms can also be singly- or doubly-substituted by D and A, so that the reversible coordinate D→A bond is formed (i) between D and A, which both constitute parts of the respective π system, or (ii) from the D or A part of the π system and the other substituent of the non-condensed π system or of the condensed-on ring system in each case, or (iii) both D and A are such substituents, wherein in the case of (iii) at least one additional D or A entity or both is (are) part of the π system or of the condensed-on ring system, M represents a transition metal of subgroups II, IV, V or VI of the periodic table of the elements (Mendeleev, including the lanthanides and actinides), X denotes an anion equivalent, and n denotes the numbers zero, one, two, three or four depending on the charge of M and on those of πI and πII.

14. A π-complex compound according to claim 4, wherein said donor atoms are selected from the group consisting of N, P, O or S.

15. A π-complex compound according to claim 5, wherein said acceptor atoms A are selected from the group consisting of B, Al or Ga.

16. A π-complex compound according to claim 7, wherein M represents Ti, Zr, Hf, V, Nb, or Ta.

17. A π-complex compound according to claim 8, wherein D is part of the ring of the associated π system.

18. The production of pure poly-(1,3-dienes) according to claim 13, wherein said poly-(1,3-dienes) comprises a high degree of 1,3-cis linking.

19. A π-complex compound according to claim 1, wherein said π-complex compound is a metallocene compound.

20. A method according to claim 2, wherein said π-complex compound is a metallocene compound.

21. A reaction product of ionizing agents with π-complexes according to claim 10, wherein said π-complex is a metallocene compound.

22. A rearrangement product formed by self-activation of π-complex compounds according to claim 11, wherein said π-complex compound is a metallocene compound.

23. The production of highly syndiotactic polystyrenes according to claim 12, wherein said π-complex compound is a metallocene compound.

24. The production of pure poly-(1,3-dienes) according to claim 13, wherein said π-complex compound is a metallocene compound.

* * * * *